(12) United States Patent
Bartynski et al.

(10) Patent No.: US 11,400,044 B2
(45) Date of Patent: Aug. 2, 2022

(54) THERMORESPONSIVE POLYMERS AND USES THEREOF

(71) Applicant: AesculaTech, Inc., Los Angeles, CA (US)

(72) Inventors: Andrew Bartynski, East Palo Alto, CA (US); Niki Bayat, Los Angeles, CA (US)

(73) Assignee: AesculaTech, Inc., Los Angeles, CA (US)

( * ) Notice: Subject to any disclaimer, the term of this patent is extended or adjusted under 35 U.S.C. 154(b) by 494 days.

(21) Appl. No.: 16/009,636

(22) Filed: Jun. 15, 2018

(65) Prior Publication Data
US 2018/0360743 A1 Dec. 20, 2018

Related U.S. Application Data

(60) Provisional application No. 62/521,188, filed on Jun. 16, 2017.

(51) Int. Cl.
A61K 9/00 (2006.01)
A61P 27/02 (2006.01)
A61K 9/08 (2006.01)
A61K 31/785 (2006.01)
C08F 220/56 (2006.01)
A61F 9/00 (2006.01)
C08F 220/54 (2006.01)
A61K 47/32 (2006.01)

(52) U.S. Cl.
CPC .......... A61K 9/0024 (2013.01); A61F 9/0017 (2013.01); A61K 9/08 (2013.01); A61K 31/785 (2013.01); A61P 27/02 (2018.01); C08F 220/54 (2013.01); C08F 220/56 (2013.01); A61F 9/0008 (2013.01); A61K 9/0051 (2013.01); A61K 47/32 (2013.01); C08F 2800/20 (2013.01)

(58) Field of Classification Search
None
See application file for complete search history.

(56) References Cited

U.S. PATENT DOCUMENTS

| | | | |
|---|---|---|---|
| 4,509,504 A | 4/1985 | Brundin | |
| 5,283,063 A | 2/1994 | Freeman | |
| 5,469,867 A | 11/1995 | Schmitt | |
| 5,830,171 A | 11/1998 | Wallace | |
| 5,840,054 A | 11/1998 | Hamano et al. | |
| 6,234,175 B1 * | 5/2001 | Zhou | A61L 27/16 128/887 |
| 8,080,593 B2 | 12/2011 | Humayun et al. | |
| 8,529,492 B2 | 9/2013 | Clauson et al. | |
| 8,640,709 B2 | 2/2014 | Odrich | |
| 8,979,821 B2 | 3/2015 | Fezza | |
| 9,089,392 B2 | 7/2015 | Clauson et al. | |
| 9,463,114 B2 | 10/2016 | Odrich et al. | |
| 9,549,846 B2 | 1/2017 | Clauson et al. | |
| 9,687,652 B2 | 6/2017 | Franke et al. | |
| 9,821,159 B2 | 11/2017 | Ackermann et al. | |
| 9,913,712 B2 | 3/2018 | Reich et al. | |
| 9,943,401 B2 | 4/2018 | De, Jr. et al. | |
| 2006/0007430 A1 | 1/2006 | Lotz et al. | |
| 2006/0134170 A1 | 6/2006 | Griffith et al. | |
| 2006/0235114 A1 * | 10/2006 | Kitazono | A61L 27/20 524/27 |
| 2006/0241751 A1 | 10/2006 | Marmo et al. | |
| 2007/0182920 A1 | 8/2007 | Back et al. | |
| 2007/0224241 A1 * | 9/2007 | Stayton | A61K 47/6933 424/423 |
| 2007/0239184 A1 | 10/2007 | Gaeckle et al. | |
| 2008/0024723 A1 | 1/2008 | Marmo et al. | |
| 2008/0140192 A1 | 6/2008 | Humayun et al. | |
| 2010/0087920 A1 | 4/2010 | Marmo | |
| 2010/0256557 A1 | 10/2010 | Lust et al. | |
| 2011/0202020 A1 | 8/2011 | Lazar | |
| 2011/0208300 A1 | 8/2011 | De, Jr. et al. | |
| 2012/0059338 A1 | 3/2012 | Beeley et al. | |
| 2012/0116504 A1 | 5/2012 | Lyons et al. | |
| 2012/0168422 A1 | 7/2012 | Boyd et al. | |
| 2012/0231072 A1 | 9/2012 | Kang-Mieler et al. | |
| 2012/0277694 A1 | 11/2012 | Odrich et al. | |
| 2012/0315265 A1 | 12/2012 | Lai et al. | |
| 2013/0101658 A1 | 4/2013 | De, Jr. et al. | |
| 2013/0118508 A1 | 5/2013 | Ainpour et al. | |
| 2013/0184661 A1 | 7/2013 | Beaton et al. | |
| 2013/0220346 A1 | 8/2013 | Lust et al. | |
| 2013/0245573 A1 | 9/2013 | De, Jr. et al. | |
| 2014/0065226 A1 | 3/2014 | Brey et al. | |
| 2014/0135918 A1 | 5/2014 | De, Jr. et al. | |
| 2015/0320596 A1 | 11/2015 | Gifford, III et al. | |
| 2016/0220725 A1 * | 8/2016 | Whalen, III | A61L 24/0015 |
| 2016/0287719 A1 | 10/2016 | Farinas et al. | |
| 2017/0157401 A1 | 6/2017 | Loudin et al. | |
| 2017/0239459 A1 | 8/2017 | Loudin et al. | |

FOREIGN PATENT DOCUMENTS

| | | | |
|---|---|---|---|
| CA | 2883874 | A1 | 10/2014 |
| CA | 159163 | S | 2/2016 |
| CN | 1145080 | A | 3/1997 |
| CN | 103747834 | A | 4/2014 |
| CN | 104921868 | | 9/2015 |

(Continued)

OTHER PUBLICATIONS

Serpe et al. "Rapidly Responding pH- and Temperature-responsive Poly(N-isopropylacrylamide)-based microgels and assemblies" ACS Omega, 2017, 2, 1769-1777. (Year: 2017).*

(Continued)

Primary Examiner — Erin E Hirt
(74) Attorney, Agent, or Firm — Thomas | Horstemeyer, LLP

(57) ABSTRACT

Compositions, methods, and kits for treating dry eye and related diseases are provided. In one aspect, the present disclosure relates to administering thermoresponsive polymeric compositions to the tear duct of the subject. Administering a thermoresponsive polymeric composition to the tear duct of the subject may be useful in treating dry eye and related conditions.

28 Claims, 9 Drawing Sheets

(56) References Cited

FOREIGN PATENT DOCUMENTS

| | | | |
|---|---|---|---|
| EP | 2490620 A1 | 8/2012 | |
| EP | 2967817 A1 | 1/2016 | |
| EP | 3209370 A1 | 8/2017 | |
| EP | 3209371 A1 | 8/2017 | |
| EP | 3209372 A1 | 8/2017 | |
| WO | WO-2008060929 A1 | 5/2008 | |
| WO | WO-2009145842 A9 | 12/2009 | |
| WO | WO-2011050327 A1 | 4/2011 | |
| WO | WO-2012123275 A1 | 9/2012 | |
| WO | WO-2013040426 A2 | 3/2013 | |
| WO | WO-2013123946 A1 | 8/2013 | |
| WO | WO-2014138085 A1 | 9/2014 | |
| WO | WO-2014138709 A1 | 9/2014 | |
| WO | WO-2015148673 A1 | 10/2015 | |
| WO | WO-2015130707 A3 | 11/2015 | |
| WO | WO-2017165449 A1 * | 9/2017 | ............ A61P 27/06 |
| WO | WO-2017192572 A1 | 11/2017 | |
| WO | WO-2018232338 A1 | 12/2018 | |

OTHER PUBLICATIONS

PCT/US2018/037899 International Search Report and Written Opinion dated Sep. 6, 2018.

Bayat et al., A reversible thermoresponsive sealant for temporary closure of ocular trauma, Science Translational Medicine, Dec. 6, 2017, vol. 9, Issue 419.

H. Zhao et al., Temperature-Sensitive poly(NIsopropylacrylamide-Co-Butyl Methylacrylate) Nanogel as an Embolic Agent: Distribution, Durability of Vascular Occlusion, and Inflammatory Reactions in the Renal Artery of Rabbits, American Journal of Neuroradiology, Aug. 2, 2012, 10.3174/ajnr.A3177.

Gandhi et al. Studies on thermoresponsive polymers: Phase behaviour, drug delivery and biomedical applications. Asian Journal of Pharmaceutical Sciences 10:99-107 (2015). Available online Aug. 28, 2014. URL:< http://dx.doi.org/10.1016/j.ajps.2014.08.010>.

CN Search Report for CN Patent Application No. 201880051718.X, dated Jul. 22, 2021.

* cited by examiner

THERMORESPONSIVE POLYMERS AND USES THEREOF

CROSS-REFERENCE

This application claims the benefit of U.S. Provisional Patent Application No. 62/521,188, filed Jun. 16, 2017, which is entirely incorporated herein by reference for all purposes.

BACKGROUND OF THE INVENTION

Dry eye syndrome (DES), also known as keratoconjunctivitis sicca (KCS), is a common eye disease that affects approximately 337 million people worldwide, with 23 million suffers over the age of 20 in the United States alone. This disease has a prevalence of 14 to 33% worldwide with an economic impact on the US up to $55 billion per year. The population of patients with eye syndrome dry includes individuals of all ages and patients present symptoms such as eye irritation, mucous discharge, fluctuating vision and decrease in lacrimal meniscus or lacrimal rupture time (TBUT). Risk factors most common include older age, female sex, medications and environments with low humidity. Dry eye is an affliction that is particularly prevalent in the elderly population, in which approximately 70% of the group is affected. Dry eye is typically characterized symptoms that may include irritation, redness, discharge, fatigued eyes, discomfort, corneal infection, scarring, and blurred vision. Dry eye occurs when either the eye does not produce enough tears (aqueous deficient dry eye) or when the tears evaporate too quickly (evaporative dry eye). Evaporative dry eye is the most prevalent type of dry eye, affecting approximately up to 86% of dry eye sufferers. Dry eye is a chronic condition that persists until treatment is provided.

The existing treatments for dry eye include artificial tears, pharmaceuticals, traditional punctal plugs (silicone or collagen), and surgery. Current treatments for dry eye suffer from a number of profound drawbacks, such as adverse side effects, high costs, invasive procedures, inconvenient application, and non-specific treatment. For patients, the average annual direct costs range from $678 for patients with mild dry eye to $1,267 for severe cases. If pharmaceuticals and traditional punctal plugs are included, the cost rises approximately to $2,959 annually. If left untreated, dry eye may lead to the scarring of the cornea.

Thus, there remains considerable need for alternative or improved treatments for dry eye.

SUMMARY OF THE INVENTION

In view of the foregoing, there exists a need for improved methods for treating dry eye and related diseases. The present disclosure provides compositions, methods and kits that address this need, and provide other advantages as well.

In some aspects, the present disclosure provides a method for occluding a channel in a subject in need thereof, the method comprising: administering a stimuli-responsive polymer to at least one channel of a subject in need; permitting the stimuli-responsive polymer to conform to the shape of the channel; activating the stimuli-responsive polymer with a trigger; wherein the trigger initiates a phase transition of the stimuli-responsive polymer from a liquid or semi-liquid to a solid or semi-solid, thereby forming a plug in the channel. The present disclosure also provides a stimuli-responsive polymer for use in a method for occluding a channel in a subject in need thereof, the method comprising: administering a stimuli-responsive polymer to at least one channel of a subject in need; permitting the stimuli-responsive polymer to conform to the shape of the channel; activating the stimuli-responsive polymer with a trigger; wherein the trigger initiates a phase transition of the stimuli-responsive polymer from a liquid or semi-liquid to a solid or semi-solid, thereby forming a plug in the channel.

In some aspects, the present disclosure provides a method for increasing tear moisture or volume in the eye of a subject in need thereof, the method comprising: administering a stimuli-responsive polymer to at least one channel of a subject in need; permitting the stimuli-responsive polymer to conform to the shape of the channel; activating the stimuli-responsive polymer with a trigger; wherein the trigger initiates a phase transition of the stimuli-responsive polymer from a liquid or semi-liquid to a solid or semi-solid, thereby forming a plug in the channel. The present disclosure also provides a stimuli-responsive polymer for use in a method for increasing tear moisture or volume in the eye of a subject in need thereof, the method being defined herein supra.

In some aspects, the present disclosure provides a method for treating or preventing dry eye in a subject in need thereof, the method comprising: administering a stimuli-responsive polymer to at least one channel of a subject in need; permitting the stimuli-responsive polymer to conform to the shape of the channel; activating the stimuli-responsive polymer with a trigger; wherein the trigger initiates a phase transition of the stimuli-responsive polymer from a liquid or semi-liquid to a solid or semi-solid, thereby forming a plug in the channel. The present disclosure also provides a stimuli-responsive polymer for use in a method for treating or preventing dry eye in a subject in need thereof, the method being defined herein supra.

In some embodiments, the stimuli-responsive polymer is selected from a group consisting of a thermoresponsive polymer, a light-responsive polymer, an ultrasound-responsive polymer, a water-responsive polymer, a biodegradable polymer and a pH-responsive polymer. In an exemplary embodiment, the stimuli-responsive polymer is thermoresponsive.

In some embodiments, the stimuli-responsive polymer at least partially fills the channel. In an exemplary embodiment, the stimuli-responsive polymer adapts to the shape of the channel.

In some embodiments, the trigger is a change in temperature, light, vibration, pH, water content, or microorganism levels. In an exemplary embodiment, the trigger is temperature.

In some embodiments, the stimuli-responsive polymer is a liquid or semi-liquid prior to administering. In certain embodiments, the stimuli-responsive polymer is a solid or a semi-solid subsequent to administering.

In some embodiments, the stimuli-responsive polymer is administered in an aqueous solution. In certain embodiments, the stimuli-responsive polymer has a concentration of about 10 weight percent to about 60 weight percent in the aqueous solution. In certain embodiments, the stimuli-responsive polymer has a concentration of about 20 weight percent to about 50 weight percent in the aqueous solution. In various embodiments, the stimuli-responsive polymer has a concentration of about 30 weight percent to about 40 weight percent in the aqueous solution.

In some embodiments, the stimuli-responsive polymer is substantially free of pathogens. In certain embodiments, the stimuli-responsive polymer is sterile.

In some embodiments, the stimuli-responsive polymer further comprises at least one excipient. In certain embodiments, the stimuli-responsive polymer further comprises at least one additive.

In some aspects, the present disclosure provides a method for occluding a channel of a subject in need, the method comprising: administering a thermoresponsive polymer to at least one channel of a subject in need; permitting the thermoresponsive polymer to conform to the shape of the channel; heating the thermoresponsive polymer; wherein the heating initiates a phase transition of the thermoresponsive polymer from a liquid or semi-liquid to a solid or semi-solid, thereby forming a plug in the channel. The present disclosure also provides a thermoresponsive polymer for use in a method for occluding a channel of a subject in need, said method being defined herein supra.

In some embodiments, the thermoresponsive polymer is a copolymer. In certain embodiments, the copolymer comprises of at least one first monomer and at least one second monomer, and wherein the first monomer and the second monomer are not the same. In certain embodiments, at least one of the first monomer and at least one of the second monomer is selected from a group consisting of N-isopropylacrylamide, N,N-diethylacrylamide, N-tert-butylacrylamide, butylacrylate, methyl vinyl ether, N-vinylcaprolactam, pentapeptide, ethylene oxide, propylene oxide, pluronic F-127, and chitosan. In various embodiments, at least one of the first monomer is N-isopropylacrylamide. In certain embodiments, at least one of the second monomer is N-tert-butylacrylamide. In certain embodiments, at least one of the second monomer is butylacrylate. For example, the first monomer may be N-isopropylacrylamide and the second monomer may be N-tert-butylacrylamide. The first monomer may be N-isopropylacrylamide and the second monomer may be butylacrylate.

In some embodiments, the first monomer and the second monomer has a weight percentage of about 99:1 to about 50:50. In some embodiments, the first monomer and the second monomer have a weight percentage of about 99:1 to about 80:20. The first monomer and the second monomer may have a weight percentage of about 95:5. In some embodiments, the first monomer is poly(N-isopropylacrylamide) and the second monomer is butylacrylate, and wherein the first monomer and the second monomer have a weight percentage of about 95:5.

In some embodiments, the thermoresponsive polymer is a liquid or semi-liquid prior to administering. In some embodiments, the thermoresponsive polymer is a solid or a semi-solid subsequent to administering.

In some embodiments, the thermoresponsive polymer is administered in an aqueous solution. In some embodiments, the thermoresponsive polymer has a concentration of about 10 weight percent to about 60 weight percent in the aqueous solution. In certain embodiments, the thermoresponsive polymer has a concentration of about 20 weight percent to about 50 weight percent in the aqueous solution. In certain embodiments, the thermoresponsive polymer has a concentration of about 30 weight percent to about 40 weight percent in the aqueous solution. In some embodiments, the thermoresponsive polymer has a concentration of about 30 weight percent in the aqueous solution.

In some embodiments, the thermoresponsive polymer is substantially free of pathogens. In certain embodiments, the thermoresponsive polymer is sterile.

In some embodiments, the thermoresponsive polymer further comprises at least one excipient. In some embodiments, the thermoresponsive polymer further comprises at least one additive.

In some embodiments, the thermoresponsive polymer has a lower critical solution temperature from about 10° C. to about 45° C. In certain embodiments, the thermoresponsive polymer has a lower critical solution temperature from about 10° C. to about 40° C. In certain embodiments, the thermoresponsive polymer has a lower critical solution temperature from about 10° C. to about 35° C.

In some embodiments, the method further comprises maintaining the thermoresponsive polymer at a temperature at least approximately below the lower critical solution temperature of the thermoresponsive polymer prior to the administering.

In some embodiments, the heating is applied from the subject's body temperature. In certain embodiments, the heating is applied from an external source. For example, the external source may be a heat pack.

In some embodiments, the channel is selected from a tear duct, a fallopian tube, a vas deferens, an artery, a blood vessel, and a lumen of a bone. In an exemplary embodiment, the channel is a tear duct.

In some embodiments, administering is in an effective amount to occlude at least one of the tear duct.

In some embodiments, the subject is a human or an animal. In certain embodiments, the subject is an animal. In an exemplary embodiment, the subject is human. In some embodiments, the subject was diagnosed with dry eye. In certain embodiments, the subject experienced at least one symptom of dry eye.

In some embodiments, the thermoresponsive polymer at least partially fills the channel. In some embodiments, the thermoresponsive polymer adapts to the shape of the channel.

In some embodiments, the method comprises inserting a dilator into the tear ducts and dilating the tear ducts prior to the administering.

In some embodiments, the method is effective in preventing dry eye. In an exemplary embodiment, the method is effective in treating dry eye. In some embodiments, the method is effective in increasing tear moisture or tear volume in the eye.

In some aspects, the present disclosure contemplates a kit for delivering a stimuli-responsive polymer, the kit comprising: an injecting device; a tear duct nozzle; a stimuli-responsive polymer described herein; and instructions for using the stimuli-responsive composition to treat a subject suffering from dry eye.

In some embodiments, the stimuli-responsive polymer is available in an aqueous solution. In some embodiments, the stimuli-responsive polymer is a thermoresponsive polymer.

In some aspects, the present disclosure contemplates a kit for delivering a thermoresponsive polymer, the kit comprising: an injecting device; the thermoresponsive polymer described herein; and instructions for using the thermoresponsive polymer to treat a subject suffering from dry eye.

In some embodiments, the thermoresponsive polymer is available in an aqueous solution. In some embodiments, the thermoresponsive polymer is a copolymer, wherein the copolymer comprises of at least one first monomer and at least one second monomer, wherein the first monomer is poly(N-isopropylacrylamide) and the second monomer is butylacrylate, wherein the first monomer and the second monomer has a weight percentage of about 95:5, and wherein the thermoresponsive polymer has a concentration of about 30 weight percent in the aqueous solution.

The present invention discloses a thermoresponsive polymer for use in a method for treating or preventing dry eye in a subject in need thereof, wherein the thermoresponsive polymer has a lower critical solution temperature from about 10° C. to about 35° C. In one embodiment, the thermoresponsive polymer is a copolymer poly(N-isopropyl acrylamide)-co-butylacrylate. In one embodiment, poly(N-isopropylacrylamide) and butylacrylate are present in the copolymer in a weight percentage of about 95:5. In one embodiment, the thermoresponsive polymer has a concentration of about 30 weight percent in an aqueous solution. In one embodiment, the subject is an old human. In one embodiment, the subject is a female. In one embodiment, the subject is an old female.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A depicts the insertion of the stimuli-responsive polymer into the inferior tear duct of a subject with an injecting device. FIG. 3B depicts the tear ducts of the subject being plugged with the stimuli-responsive polymer. FIG. 3C depicts the tear ducts of the subject that have been occluded.

FIG. 4A depicts the insertion of the stimuli-responsive polymer into the superior tear duct of a subject with an injecting device. FIG. 4B depicts the tear ducts of the subject being plugged with the stimuli-responsive polymer. FIG. 4C depicts the tear ducts of the subject that have been occluded with the stimuli-responsive polymer.

FIG. 5A depicts the human eye and the associated lacrimal drainage system prior to the insertion of the punctal plug. The tear ducts of the subject do not contain the stimuli-responsive polymer. FIG. 5B depicts an injecting device inserting the stimuli-responsive polymer into the tear ducts of the subject. FIG. 5C depicts the tear ducts of the subject that have been occluded with the stimuli-responsive polymer.

DETAILED DESCRIPTION OF THE INVENTION

Figure 1:
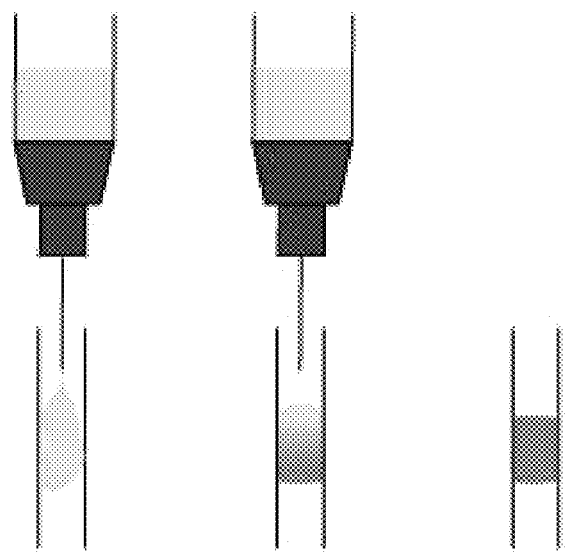
FIG. 1 is a schematic representation of occluding a channel with a stimuli-responsive polymer.
Figure 2:
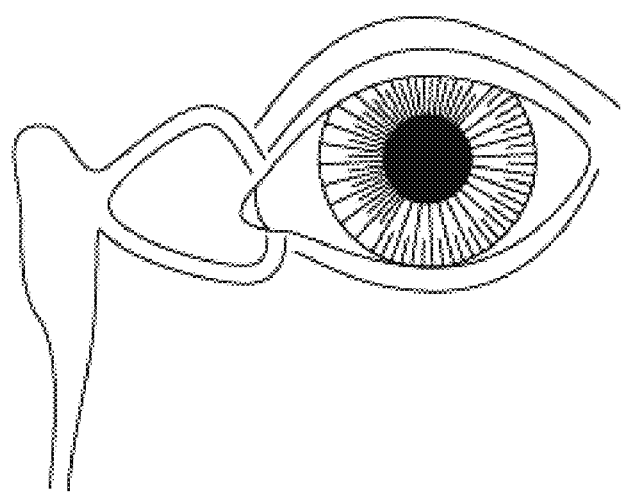
FIG. 2 is an anatomical drawing of the human eye and its lacrimal drainage system.
Figure 3A:
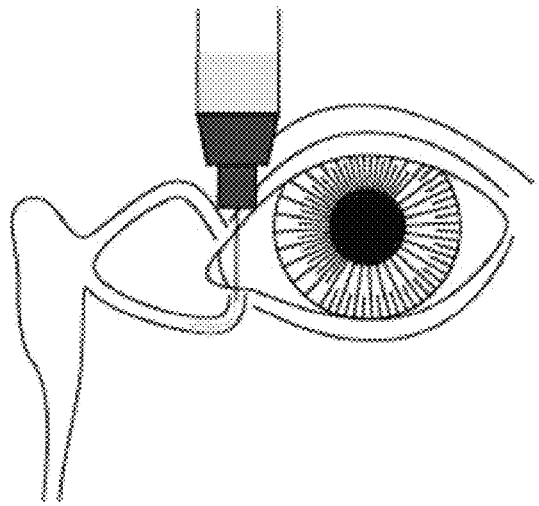
FIG. 3A-FIG. 3C are schematic representations of the insertion procedure for the punctal plug into the inferior tear duct.
Figure 3B:
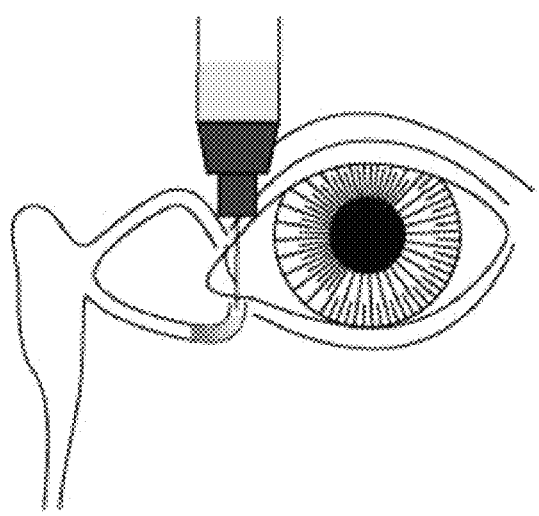
Figure 3C:
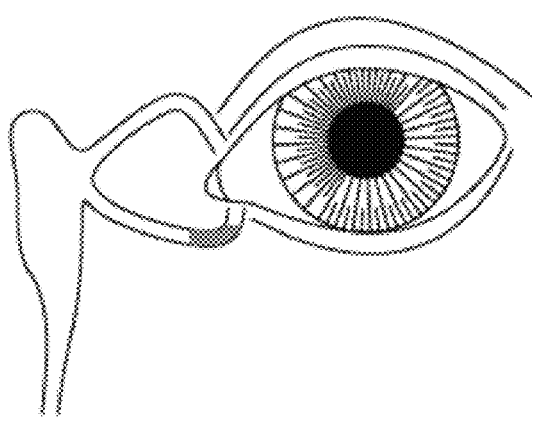
Figure 4A:
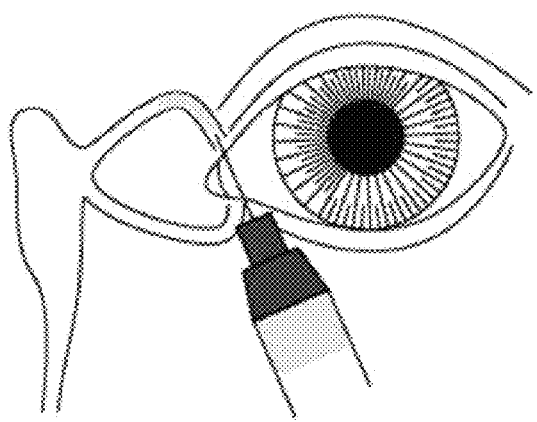
FIG. 4A-FIG. 4C are schematic representations of the insertion procedure for the punctal plug into the superior tear duct.
Figure 4B:
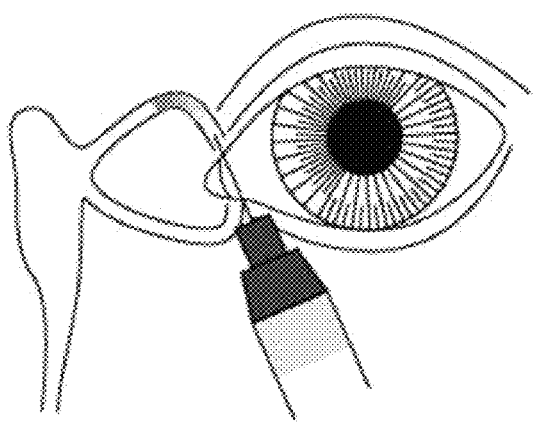
Figure 4C:
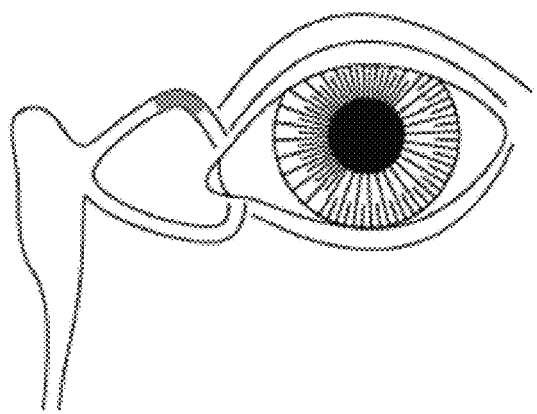
Figure 5A:
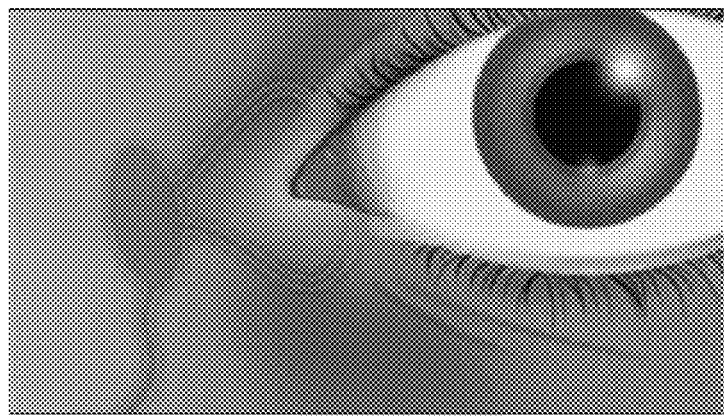
FIG. 5A-FIG. 5C are schematic representations of the insertion procedure of the punctal plug with an injecting device.
Figure 5B:
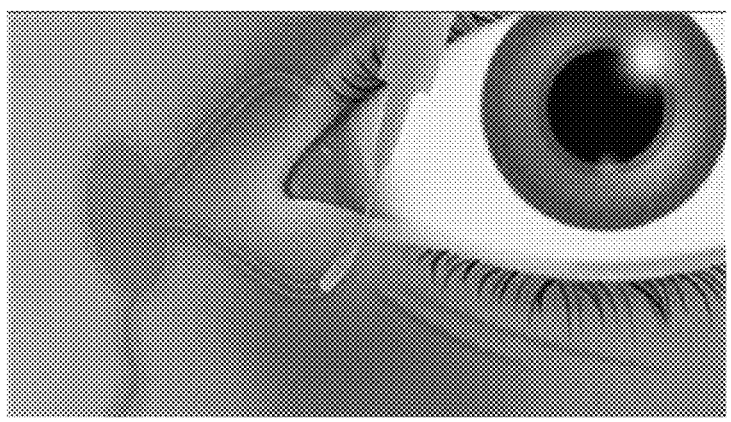
Figure 5C:
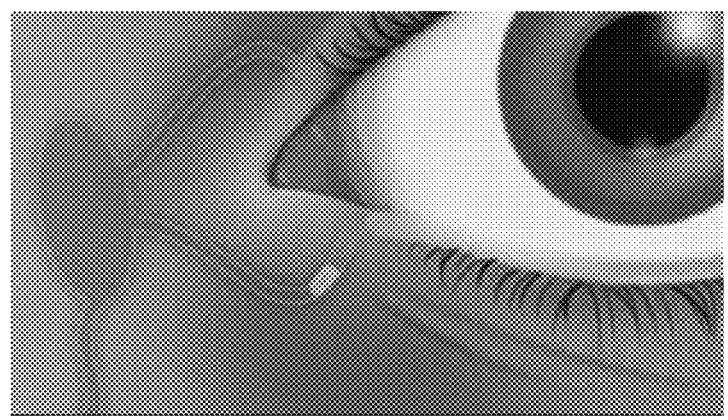

The present disclosure relates to ophthalmic compositions and methods useful in treating human or animal eyes. In one aspect, the present disclosure relates to administering thermoresponsive polymeric compositions to the tear duct of the subject. Administering a thermoresponsive polymeric composition to the tear duct of the subject may be useful in treating dry eye and related conditions.

Definitions

Unless otherwise stated, the following terms used in this application have the definitions given below. The section headings used herein are for organizational purposes only and are not to be construed as limiting the subject matter described.

The term "polymer" as used herein may refer to a homopolymer, a copolymer, a tri-polymer and other multi-polymer, or a mixture thereof.

The term "lower critical solution temperature" (LCST) or "lower consolute temperature" is the critical temperature below which a thermoresponsive polymer is miscible for all compositions.

The term "upper critical solution temperature" (UCST) or "upper consolute temperature" is the critical temperature above which a thermoresponsive polymer is miscible in all proportions.

The terms "prevent," "preventing," or "prevention" refer to providing treatment prior to the onset of a condition. If treatment is commenced in subjects with a condition, such treatment is expected to prevent, or to prevent the progression of, the medical sequelae of the condition.

The term "subject" or "individual" as used herein includes mammals. Non-limiting examples of mammals include humans, dogs, cats, and mice, including transgenic and non-transgenic mice. The methods described herein can be useful in both human therapeutics, pre-clinical, and veterinary applications. In some embodiments, the subject is a mammal, and in some embodiments, the subject is human.

The term "tear duct" or "tear ducts" as used here in refers to any portion of the lacrimal system, such as puncta, canaliculi, lacrimal sac, and lacrimal duct.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Dry eye is a condition in which an individual does not maintain sufficient amounts of tears to lubricate and nourish the eye. Tears are particularly important in maintaining the health of the front surface of the eye and for providing clear vision; tears provide lubrication, reduce the risk of eye infection, and wash away foreign matter in the eye. Those with dry eyes may experience irritated, gritty, scratchy or burning eyes; a feeling of something in their eyes; excess watering; and blurred vision.

Dry eye can be a temporary or chronic condition. Dry eyes may develop for a number of reasons, which include: age, gender, medications, medical conditions, environmental conditions, long-term use of contact lenses. For example, dry eye may be a common side effect of some medications, such as antihistamines, nasal decongestants, tranquilizers, certain blood pressure medicines, Parkinson's medications, birth control pills and anti-depressants. Also, dry eye can be associated with diseases of the glands, and immune system disorders, such as Sjögren's syndrome, lupus, and rheumatoid arthritis.

Dry eyes can occur when secretion and excretion—i.e. tear production and tear drainage—in the lacrimal system is not in balance. The lacrimal system is divided into the secretory component or the lacrimal gland, and the excretory components that make up the lacrimal outflow system. The lacrimal outflow system includes the puncta, the ampulla, the upper canaliculus, the lower canaliculus, common canaliculus, lacrimal sac, and nasolacrimal duct. Tears enter the puncta to be eliminated through the lacrimal sac into the nose.

There are several clinical tests to evaluate the patients with dry eye symptoms, which include: dye staining in the ocular surface, tear rupture time, Schirmer test, test Fluorescein clearance, lacrimal gland function and lacrimal osmolarity. Based on these clinical measures and patient's symptoms it is possible diagnose and classify the disease. Dry eye is classified as mild, moderate and severe according to symptoms and evaluation of clinical signs. Due to the nature of the disease, classification is imprecise because the characteristics of each level overlap.

In patients with moderate to severe dry eye, the occlusion of the lacrimal puncta is an attractive method to increase the height (amount) of the tear meniscus and provide symptomatic relief. Currently, removable silicone plugs are the standard for long-term treatment and, in some cases, can be preserved for extended periods without complications. A critical problem with the existing tear duct plugs in the market is its spontaneous extrusion rate (loss). Thus, it is recommended that patients with lacrimal plugs are monitored regularly to make sure that the plugs are still present in their place and in the correct position. There is further a need for technical solutions in treating dry eye that require fewer administrations, interventions, or monitoring.

Traditional tear plugs are made in predetermined sizes. The doctor must use standard sizes and choose a size that best suits an individual. In some cases, the size of the plug may be inappropriate, e.g. too tight or loose, which may cause the plug to eventually migrate through the tear duct or leave the lacrimal point. To address these concerns, the present disclosure provides an adaptable tear plug. The adaptable tear plug may be inserted into the body as a liquid and solidify in situ, thereby allowing the plug to fit the specific anatomy of each patient.

Compositions and methods of the present disclosure aim to restore or maintain the normal amount of tears in the eye to minimize dryness and related discomfort, and to maintain eye health. The compositions and methods may restore the balance of secretion and excretion in the lacrimal system.

Compositions

The present disclosure provides for activatable polymers that change their physical properties upon a known stimulus. Preferably, such polymers (herein refers to polymer or hydrogel thereof) are activatable between a delivery state and a therapeutic state. In some instances, a polymer can be activatable between a therapeutic state and a release state.

In the delivery state, the polymers herein are preferably liquid or semi-liquid (e.g., gel) in form. This allows them to be easily delivered into an orifice or channel in a body of an individual. In this embodiment, the therapeutic state is preferably a solid state. In the release state, the polymers are preferably liquid or semi-liquid, which allows the polymers to easily be removed.

In other embodiments, the delivery state and the therapeutic state can be a solid state and the release state can be a liquid state. The liquid release state allows the polymers to easily be removed.

Once located in the body, the activatable polymers can change into a therapeutic state, as described further below.

Activatable polymers include stimuli-responsive polymers and thermoresponsive polymers.

Stimuli-responsive polymers, also known as "smart polymers," are polymers that respond to their environment by changing their physical and/or chemical properties. A stimuli-responsive polymer can be one that responds to one or more stimuli, including pH, light, temperature, humidity, mechanical force, the presence of small molecule or biomolecule, electronic fields and/or magnetic fields.

Examples of stimuli-responsive polymers include, but are not limited to, thermoresponsive polymers, light-responsive polymers, ultrasound-responsive polymers, water-responsive polymers, biodegradable polymer, pH-responsive polymers, and combinations thereof.

Stimuli-responsive polymer may respond to changes in the environment. Such changes in the environment can induce small to large changes in the stimuli-responsive polymer's properties. Upon responding to at least one stimulus, a stimuli-responsive polymer can, e.g., change shape, color or transparency, become conductive, or become permeable to water. In an exemplary embodiment, a polymer of the disclosure is one that changes its shape in response to at least one stimulus such as temperature. More preferably, a polymer herein transforms from a temporary shape (e.g., that of a liquid or solution) to a permanent shape (e.g., that of a solid). In some embodiments, a polymer herein transforms from a soft to a hard material, or from an elastic to rigid material.

Preferably embodiments contemplate thermoresponsive polymers. Thermoresponsive polymers are polymers that exhibit a change of their physical properties with temperature. In some embodiments, a thermoresponsive polymer can have a drastic and discontinuous change to its physical property occur with a change of environmental temperature. In some embodiments, a thermoresponsive polymer exhibits a volume phase transition at a certain temperature. This transition can be reversible or irreversible. In an exemplary embodiment, the transition is reversible. In some embodiments, a thermoresponsive polymer becomes insoluble at a lower critical solution temperature (LCST). In some embodiments, a thermoresponsive polymer is one that becomes soluble upon heating and has an upper critical solution temperature (UCST).

In certain embodiments, a composition is a blend of two or more different polymers. For example, a composition can comprise a mixture of a first polymer and a second polymer, where each is different.

In certain embodiments, a composition comprises one or more copolymers. A copolymer is a polymer having two or more different types of monomers joined in the same polymer chain. In certain embodiments, a composition herein comprises a block copolymer. Block copolymers are made up of blocks of different polymerized monomers. In certain embodiments, a composition herein comprises a random copolymer. Random copolymers are made up of repeating units that are dispersed irregularly along the linear chains. In certain embodiments, a composition herein comprises cross-linked copolymers. Cross-linked copolymers are polymers that are linked to one another by covalent or ionic or hydrogen bonds.

Examples of polymers contemplated herein include the following: poly(N-alkylacrylamide), poly(N-vinyl caprolactam), poly(N-ethyl oxazoline), poly(methyl vinyl ether), poly(acrylic acid-co-acrylamide), poly(N-tert-butylacrylamide), poly(butylacrylate), and elastin-like oligo- and poly-peptides. For example, such thermoresponsive monomers may include N-isopropylacrylamide (NIPAM), N-[2-(diethylamino)ethyl acrylamide] (DEAEAM), N,N-(dimethylaminoethyl methacrylate) (DMAEMA), (N,N-(diethylaminoethyl methacrylate) (DEAEMA), poly(-(N-morpholine) ethyl methacrylate) (MEMA), oligo(ethylene glycol) methacrylate, (N,N-diethylacrylamide) (DEAAM), N-tert-butylacrylamide, butylacrylate, methyl vinyl ether, N-vinylcaprolactam, poly(pentapeptide) of elastin, ethylene oxide, propylene oxide, pluronic F-127, hydroxypropylcellulose, and chitosan. In certain embodiments, the thermoresponsive polymer comprises at least NIPAM. In an exemplary embodiment, the thermoresponsive polymer comprises NIPAM and N-tert-butylacrylamide. In an exemplary embodiment, the thermoresponsive polymer comprises NIPAM and butylacrylate.

Any of the polymers described herein can be available as a copolymer. The copolymer can be a thermoresponsive polymer comprising a first monomer and a second monomer, such as NIPAM and butylacrylate with a weight percentage of about 99:1 to about 50:50. In some embodiments, the weight percentage of the first monomer and second monomer, such as NIPAM and butylacrylate, can be between 99:1 and 70:30, 99:1 and 80:20, 98:2 and 85:15, 98:2 and 90:10, 98:2 and 91:9, or 97:3 and 92:8. The weight percentage can be 98:2, 97:3, 96:4, 95:5, 94:6, 93:7, 92:8, 91:9, 90:10, 85:15, 80:20, 75:25, or 70:30. In an exemplary embodiment, the first monomer and the second monomer have a weight percentage of 95:5, such as 95:5 of NIPAM and butylacrylate by weight percent. In some embodiments, the copolymer comprises at least 80, 85, 90, 91, 92, 93, 94, 95, 96, 97, 98 or 99% of NIPAM by weight.

The polymers described above can be combined to create a composition having two or more polymers. The polymers above can be combined to create block copolymers, random copolymers, and cross-linked copolymers.

In some embodiments, a block copolymer herein comprises any of the above or the following block monomers: N-isopropylacrylamide, N,N-diethylacrylamide, N-tert-butylacrylamide, butylacrylate, methyl vinyl ether, N-vinylcaprolactam, poly(pentapeptide) of elastin, ethylene oxide, propylene oxide, pluronic F-127, and chitosan. In some embodiments, at least one of the first block monomer may be N-isopropylacrylamide. In one embodiment, at least one of the second block monomer is N-tert-butylacrylamide. In another embodiment, first block monomer is N-isopropylacrylamide and the second monomer is N-tert-butylacrylamide. In one embodiment, at least one of the second block monomer is butylacrylate. In an embodiment, a first block monomer is N-isopropylacrylamide and a second block monomer is butylacrylate.

In some embodiments, monomers of any of the polymers described herein can be used to create a copolymer of individual monomers.

When creating a copolymer or block copolymer, the polymer may be multi-responsive in which the stimuli-responsive polymer comprises at least one thermoresponsive polymer and at least one other stimuli-responsive polymer. Multi-responsive polymers may be synthesized by incorporating other functional groups into the temperature responsive polymer. For example, pH responsive compounds that have ionizable functional groups capable of donating or accepting protons upon environmental pH changes may be used. In some embodiments, the stimuli-responsive polymer comprises a thermoresponsive polymer and a pH responsive polymer. In one embodiment, the stimuli-responsive polymer comprises acrylic acid (AAc) and N,N-dimethylaminoethyl methacrylate (DMAEMA). In some embodiments, the stimuli-responsive polymer comprises a thermoresponsive polymer and a light responsive polymer. In some embodiments, the stimuli-responsive polymer comprises a thermoresponsive polymer and an enzyme responsive polymer.

Any of the polymers herein can be formulated in an aqueous solution at a concentration from 10-90 weight percent. The polymer can be formulated in an aqueous solution at a concentration from 15-80 weight percent, 20-70 weight percent, 20-60 weight percent, 20-50 or 20-40 weight percent. In some embodiments, the concentration of polymer is 20-40% by weight. The polymer can be formulated in an aqueous solution at a concentration of at least 15%, at least 20%, at least 25%, at least 30%, at least 35%, at least 40%, at least 45%, or at least 50%. The polymer can be formulated in an aqueous solution at a concentration of no more than 80%, 75%, 70%, 65%, 60%, 55% or 50%. In some embodiments, the polymer can be a copolymer comprising a first monomer and a second monomer, and the copolymer is formulated in an aqueous solution at a concentration of 20-60 weight percent, such as approximately 20%, 25%, 30%, 35%, 40%, 45%, 50%, 55%, or 60%. In some embodiments, the concentration of the copolymer in aqueous solution can be 20-50% by weight and the copolymer comprising a first monomer and a second monomer, such as NIPAM and butylacrylate, with a weight percentage of approximately 99:1 to 90:10. In an exemplary embodiment, the weight percent of the copolymer in water is 30%. For example, the copolymer can be formulated at a concentration of 30% w/w in water with a thermoresponsive polymer comprising NIPAM and butylacrylate (95:5 w/w).

When the two homopolymers, crosslinked homo/copolymers, block copolymers, and/or copolymers are mixed, a first and a second polymer may have a weight percentage that varies depending on the desirable properties. In some embodiments, the first polymer is a stimuli-responsive polymer. The stimuli-responsive polymer may represent approximately 50% or more of the mixture.

When two or more polymers, block copolymers, and/or copolymers are used, a first monomer and a second monomer have a number average molecular weight of about 5,000 to about 5,000,000 Daltons. In some embodiments, the first monomer and the second monomer have a number average weight of about 5,000 to about 5,000,000 Daltons. In a preferred embodiment, the first monomer and the second monomer have a number average weight of about 5,000 to 50,000 Daltons.

The performance of the occluding thermoresponsive polymer may be dependent on the lower critical solution (LCST) of the polymer. In certain embodiments, the thermoresponsive polymer has a lower critical solution temperature from about 5° C. to about 40° C., about 10° C. to about 40° C., or about 10° C. to about 35° C. In one embodiment, the thermoresponsive polymer has a lower critical solution temperature of about 5° C. to about 40° C. The thermoresponsive polymer may have a lower critical solution temperature of 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. In an exemplary embodiment, the thermoresponsive polymer has a LCST of about physiological body temperature. Body temperature can also include eye temperature.

Uses

Any of the activatable polymers herein can be used to occlude or partially block an orifice, for example for in vivo therapeutic uses. Such orifice can be a channel. Such channel can be a tear duct. Other examples of channels that can be occluded or partially blocked include a fallopian tube, a vas deferens, an artery, a blood vessel, and a lumen of a bone. The compositions herein can be used to occlude the orifice or channel thus prohibiting the transfer of liquid or solid compositions in the body. Any of the compositions described herein can be used to treat or prevent dry eye in a subject in need thereof by occluding at least one tear duct. Any of the compositions described herein can be used to occlude at least one tear duct and increase moisture retention in a subject in need thereof in at least one eye.

In an exemplary embodiment, an activatable polymer herein is administered to a tear duct of a subject in liquid or semi-liquid form. The polymer, such as copolymer NIPAM and butylacrylate (95:5 w/w), can be administered to the tear duct to treat or prevent dry eye. Upon contact with the subject's skin, or in response to the subject's body temperature, the polymer is activated which results in a phase change converting the polymer into solid form.

The polymer's viscous properties are temperature dependent. The polymer can be viscous near the subject's body temperature, for example at approximately 37° C. and can be non-viscous at room temperature, for example at approximately 25° C. The polymer can become more viscous upon insertion into a channel of the subject. Upon heating in the channel, the polymer can become more viscous, so as to occlude a channel in the subject. The polymer can maintain its viscous property at approximately body temperature or higher, and can reach its final desired state at approximately body temperature or higher. In some embodiments, the viscosity of the polymer in the channel is greater than approximately 250 Pa*s. In certain embodiments, the viscosity of the polymer in the channel is greater than approximately 1000 Pa*s. The viscosity of the polymer can be lowered by reducing the temperature of the polymer, such as by applying cold saline or a cold pack to the channel or portions of the channel. At a lower temperature, the polymer becomes more fluid and may be easily removed from the channel.

The present disclosure contemplates occluding a channel in the body of a subject in need thereof by administering a stimuli-responsive polymer to at least one channel of a subject; permitting the stimuli-responsive polymer to conform to the shape of the channel; and activating the stimuli-responsive polymer with a trigger, wherein the trigger initiates a phase transition of the stimuli-responsive polymer from a liquid or semi-liquid to a solid or semi-solid, thereby forming a plug in the channel. The trigger can be an external trigger such as light of a particular wavelength or application of particular temperature to the local site of the polymer.

In some embodiments, the polymers herein can have a reverse phase and return to a liquid or semi-liquid state upon a second activation. The second activation can be the same or different than the first activation. For example, a second activation can result from a change in pH, temperature, mechanical force, the presence of small molecules and biomolecules, electronic/magnetic fields, light, vibration, water content, microorganism levels, and/or combinations thereof.

Preferably, the second activation results from a stimulus external to the subject being treated by the composition herein.

Prior to the administration of any of the polymers herein, such polymers may be maintained at a temperature below the lower critical solution temperature of the respective composition e.g., below human body temperature. This can be accomplished using a temperature-controlled device, such as a refrigerator or a freezer. In some instances, a polymer herein is maintained at a temperature below 10° C.

In certain embodiments, the stimuli-responsive polymer or the thermoresponsive polymer is subject to a temperature change, such as an increase in temperature, subsequent to administration of either composition to the subject. In some embodiments, the thermoresponsive polymer is heated. Such heating may be applied from an external source, an internal source, or both. An external source may include heating pads, heating patches, chemical solutions, a compress, and aqueous solutions. An internal source may include the subject's body temperature. The heat may be applied near or at the channel of interest. Heating may raise the temperature of the stimuli-responsive polymer or the thermoresponsive polymer to a temperature at least about the lower critical solution temperature of either composition.

As described in the methods herein, a composition of the present disclosure may be administered to a subject in need. In certain embodiments, a stimuli-responsive polymer or a thermoresponsive polymer is administered in an effective amount to occlude at least one of the tear ducts. In some embodiments, the composition is administered directly into the channel of interest. In some embodiments, the composition is administered to the surrounding area of the channel of interest. The composition may passively enter into and occlude the channel of interest, such as a duct of the eye. The composition may be inserted in the puncta, the canaliculi, the lacrimal sac, or the nasolacrimal duct. In certain embodiments, the composition is inserted into the channel as a liquid or semi-liquid prior to administering and the composition is a solid or a semi-solid subsequent to administering. The composition may be administered using an apparatus or device with the capability to transfer a liquid or semi-liquid composition, such as a syringe or injector. For example, insertion of the plug may include locating the tear duct, inserting the injecting device into the tear duct, injecting the composition into the tear duct, allowing the composition to solidify, removing the injecting device from the tear duct, and inspecting the composition. The plug solidifies in situ due to heat from the subject's body.

The composition may be administered so as to occlude or seal a channel of interest. The composition may be administered so that the outflow of liquid through the lacrimal outflow system is prevented. The composition may be administered so that the tear duct is at least partially occluded. In one embodiment, the outflow of liquid within the lower canaliculus is prevented. The composition may be inserted into the puncta or the canaliculus. In certain embodiments, the stimuli-responsive polymer or the thermoresponsive polymer is administered so as to at least partially fill the inner cross section of at least one tear duct. In one embodiment, the stimuli-responsive polymer or the thermoresponsive polymer has an outer cross section that is less than the inner cross section of the canaliculus to at least partially seal the canaliculus. In one embodiment, the stimuli-responsive polymer or the thermoresponsive polymer has an outer cross section that is less than the inner cross section of the puncta to at least partially seal the puncta. In certain embodiments, the stimuli-responsive polymer or the thermoresponsive polymer is administered in amount ranging from about 0.1 to about 1 cc. For example, the amount administered may be 0.1, 0.2, 0.3, 0.4, 0.5, 0.6, 0.7, 0.8, 0.9, or 1 cc. The amount administered can be approximately 10-500 µL, 10-300 µL, or 10-100 µL. In some embodiments, the amount administered is 10-100 µL. The amount administered can be at least 10 µL, 50 µL, 100 µL, 150 µL, 200 µL, 250 µL, or 300 µL. The stimuli-responsive polymer or the thermoresponsive polymer may be administered so that stimuli-responsive polymer or the thermoresponsive polymer does not run on the lid to irritate the eye. In certain embodiments, the stimuli-responsive polymer or the thermoresponsive polymer may be re-administered as needed. In some embodiments, re-administration is not necessary.

In certain embodiments, the method further comprises maintaining the thermoresponsive polymer at a temperature at least approximately below the lower critical solution temperature of the thermoresponsive polymer prior to administering. In some embodiments, the thermoresponsive polymer is maintained at a temperature below 40° C.

Prior to administration of the stimuli-responsive polymer or the thermoresponsive polymer, the method may further comprise applying a local anesthetic. Local anesthetics may include Akten®, Alcaine®, Altacaine®, Ocu-Caine®, Opthetic®, Parcaine®, and TetraVisc®.

Prior to administration of the stimuli-responsive polymer or the thermoresponsive polymer, the method may further comprise inserting a dilator into the tear ducts and dilating said tear ducts prior to said administering. For example, the method may further comprise inserting a lacrimal punctal dilator into the punctum and stretching the punctum.

In certain embodiments, the composition adapts to the shape of the channel. The composition may take the form of the channel, such as the tear duct. The composition may vary from subject to subject, and from channel to channel. In certain embodiments, the composition molds into place without abrading the tear duct or forming rough edges thereon. For example, the composition may mold into the canaliculus interior surface. In certain embodiments, the composition conforms to the interior of the canaliculus to form an occlusion inside the lacrimal outflow system. In some embodiments, the composition is added until constrained by the inner surface of the canaliculus.

In certain embodiments, the composition forms a plug subsequent to activating a trigger, such as increasing temperature. In some embodiments, the plug of the composition is positioned in the tear ducts to stop the egress of tears from the eye. In some embodiments, the plug of the composition allows the tears to stay on the surface of the eye.

In certain embodiments, the subject is a human or an animal. In one embodiment, the subject is human. In one embodiment, the subject is an animal. In certain embodiments, the subject was diagnosed with dry eye. In certain embodiments, the subject experience at least one symptom of dry eye. In certain embodiment, treating or preventing dry eye means to increase or maintain the amount of moisture in the eye of the subject. For example, the subject may increase moisture in at least one eye by at least about 5%, at least about 10%, at least about 15%, at least about 20%, at least about 25%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100% when compared to the level observed in biologically matched control subject or specimen that was not administered said stimuli-responsive polymer or thermoresponsive polymer. In some embodiments, the moisture is in the form of natural tears. In some embodiments, the moisture is in the form of artificial tears. In some embodiments, the moisture is in the form of medicated eye drops.

The subject treated with the compositions described herein can sustain an improvement with their Schirmer Tear Test (STT) results. Prior to treatment, the subject may have "severe" or "moderate" STT results. Upon treatment with the thermoresponsive device, the subject can obtain "moderate," "mild," or "normal" STT results. The subject can observe results that are at least greater than 4 mm wetting of the paper, such as 4, 5, 6, 7, 8, 9, 10, 11, 12, 13, 14, 15, 16, 17, 18, 19, or 20 mm.

The subject treated with the compositions described herein can maintain normal intraocular pressure (TOP). Upon treatment with the thermoresponsive device, the subject can maintain normal TOP. In some embodiments, the subject has an TOP approximately between 10-21 mm Hg, such as approximately 10, 11, 12, 13, 14, 15, 16, 17, 18, 19, 20, or 21 mm Hg.

The subject treated with the compositions herein can be human, such as an adult or child. The subject treated with the compositions herein can be an elderly subject (e.g., over 65 years of age). The subject can be a female. The subject can be an old female. A female subject may be pregnant or on hormone replacement therapy. The subject can be a male. The subject can be taking one or more medications, such as anti-histamines, nasal decongestants, tranquilizers, blood pressure medicines, Parkinson's medications, birth control or anti-depressants. The subject can have a skin disease on or around the eyelids. The subject can have a disease of the glands in the eyelids, such as Meibomian gland dysfunction. The subject may have undergone a refractive surgery, such as LASIK. The subject may have experienced chemical or thermal burns. In certain embodiments, the subject has been diagnosed with chronic inflammation of the conjunctiva. In certain embodiments the subject has been diagnosed with keratitis. In an exemplary embodiment, the subject has been diagnosed or experiences one or more symptoms or conditions of dry eye. In some embodiments, the subject treated with the compositions herein is an animal.

The methods provided herein may be used for treating a disease or condition that would benefit from increasing or maintain moisture in the eyes. Such methods involve administering to a subject in need thereof any of the activatable polymers described herein. When delivered, such polymers are in their delivery state. After delivery the polymers change to a therapeutic state. The changing of the delivery state to the therapeutic state can be automatic, such as by body heat of the subject. Alternatively, such change can occur only upon application of a particular external trigger, such as a particular radiation wavelength or radio wavelength. In some instances the delivery state is one of liquid or semi-liquid and the therapeutic state is solid (or semi solid). In other instances, the delivery state is solid (or semi-solid), and the therapeutic state is liquid or semi-liquid.

Preferably, the methods and compositions provided herein are effective in preventing dry eye and maintaining moisture in the eye. Such methods and compositions can be effective in providing immediate relief to the eye as well as long-term relief.

When occluding a tear duct, subsequent to solidification, the polymer herein forms a plug. The plug may be visible using the naked eye. The plug may be visible using a microscope, magnifying glass, or a magnifying instrument. In certain embodiments, the plug may not be visible to the naked eye.

The plug may be removed by mechanical means or by application of a stimulus. Mechanical means include the use of forceps or an applicator tip. For example, mechanical removal of the plug may include locating the plug, inserting the forceps into the channel, engaging the plug, removing the plug, and checking for patency of the channel. Stimuli removal involves apply a stimulus to the plug, such as with cold fluid or a cold pack, thereby causing the plug to dissolve. In some embodiments, the cold fluid is approximately less than 15° C. The cold fluid may be water, saline solution, mineral oil, and the like. In some embodiments, any of the triggers described herein can be used to dissolve a plug. For example, stimuli removal may include locating the plug, flushing the channel with cold saline, and checking the channel for patency of the channel.

Formulations

The polymers herein can be formulated with a pharmaceutically acceptable excipient. The composition may also contain one or more excipients, stabilizers, additives or the like. In one embodiment, the pharmaceutically acceptable excipient is suitable for ophthalmic administration. The composition may be substantially free of pathogens. The composition may have less than about 10%, less than about 5%, less than about 1%, less than about 0.5%, less than 0.1% or even less of a specified component. The composition may be sterilized, for example, with ethylene oxide, prior to administration.

Kit

Contemplated herein are kits. Such kit can include one or more of the following: a syringe or injector; a tear duct needle or nozzle; a stimuli-responsive polymer/copolymer/block copolymer; and instructions for use, such as for occluding a tear duct to treat dry eyes. Preferably, the polymer/copolymer/block copolymer is in a prefilled syringe and is exclusively in the kit. The polymer/copolymer/block copolymer may be in an aqueous solution or be provided along with instructions on how to activate it into a liquid or semi-liquid state (delivery state). The kit may include any composition described herein. For example, the kit may contain a thermoresponsive composition that is a copolymer. The copolymer may comprise poly(N-isopropylacrylamide) and butylacrylate, wherein the copolymer has a weight percentage of about 95:5 (NIPAM: butylacrylate), and wherein said thermoresponsive polymer has a concentration of about 30 weight percent in said aqueous solution.

Therapeutic Applications

The compositions and methods described herein can be used to treat any mammal including a human. In some instances, the compositions herein are used to treat a non-human mammal, such as a domesticated animal.

The compositions and methods described herein can be useful as a therapeutic, for example, for the treatment of dry eye condition, thereby resulting in a reduction, suppression, remission, or eradication of symptoms.

In some instances, the composition herein is used to prevent a disease or condition, such as dry eye condition. For example, an individual at risk of developing dry eyes can be administered any of the compositions herein for the purpose of occluding or partially blocking their tear ducts.

Other conditions which the compositions herein can be used to treat or prevent include, but are not limited to, age-related macular degeneration (AMD), keratoconjunctivitis sicca (KCS), dysfunctional tear syndrome, lacrimal keratoconjunctivitis, evaporative tear deficiency, aqueous tear deficiency, and LASIK-induced neurotrophic epitheliopathy (LNE). The compositions and methods provided herein can be useful for the treatment of glaucoma or other related diseases that would benefit from being able to control the pressure on the eye.

The compositions and methods provided herein can be used in combination with other pharmaceutical agents, which include antibacterial, antiviral, antifungal, anti-VEGF, growth factor, immunosuppressive, and anti-inflammatory agents.

EXAMPLES

Example 1

Synthesis of Copolymer of NIPAM:Butylacrylate 95:5

N-isopropylacrylamide (NIPAAM, 0.95 g), butylacrylate (0.05 g) and 2,2'-azobisisobutyronitrile (AIBN, 0.01 g) were dissolved in 10 mL dioxane. The solution was degassed with nitrogen for 15 minutes and then heated to 70° C. for 16 hours under inert atmosphere. The reaction mixture was allowed to cool and then added to hexanes, dropwise, to precipitate the polymer. The precipitate was filtered, washed with hexanes, and dried to yield the copolymer.

Example 2

Synthesis of Copolymer of NIPAM:Butylacrylate 95:5

N-isopropylacrylamide (NIPAAM, 0.95 g), butylacrylate (0.05 g) and 2,2'-azobisisobutyronitrile (AIBN, 0.01 g) were dissolved in 10 mL THF. The solution was degassed with nitrogen for 15 minutes and then heated to 50° C. for 16 hours under inert atmosphere. The reaction mixture was allowed to cool and then added to hexanes, dropwise. The precipitate was filtered, washed with hexanes, and dried to yield the copolymer.

Example 3

Synthesis of Copolymer of NIPAM:Butylacrylate 95:5

N-isopropylacrylamide (NIPAAM, 0.95 g), butylacrylate (0.05 g), methylene bisacrylamide (0.02 g) and 2,2'-azobisisobutyronitrile (0.01 g) were dissolved in 10 mL dioxane. The solution was degassed with nitrogen for 15 minutes and then heated to 70° C. for 16 hours under inert atmosphere.

The reaction mixture was allowed to cool and then added to hexanes, dropwise. The precipitate was filtered, washed with hexanes, and dried to yield the copolymer.

Example 5

Synthesis of Copolymer of NIPAM: 1,1,1,3,3,3-Hexafluoroisopropyl Acrylate 97:3

N-isopropylacrylamide (NIPAAM, 0.97 g), 1,1,1,3,3,3-Hexafluoroisopropyl acrylate (0.03 g), and 2,2'-azobisisobutyronitrile (AIBN, 0.01 g) were dissolved in 10 mL dioxane. The solution was degassed with nitrogen for 15 minutes and then heated to 70° C. for 16 hours under inert atmosphere. The reaction mixture was allowed to cool and then added to hexanes, dropwise. The precipitate was filtered, washed with hexanes, and dried to yield the copolymer.

Example 6

Synthesis of Copolymer of NIPAM:Butylacrylate 90:10

N-isopropylacrylamide (NIPAAM, 0.90 g), butylacrylate (0.10 g), and 2,2'-Dicumyl peroxide (0.01 g) were dissolved in 10 mL dioxane. The solution was degassed with nitrogen for 15 minutes and then heated to 70° C. for 16 hours under inert atmosphere. The reaction mixture was allowed to cool and then added to hexanes, dropwise. The precipitate was filtered, washed with hexanes, and dried to yield the copolymer.

Example 7

Synthesis of Copolymer of NIPAM:2-Ethylhexyl Acrylate 95:5

N-isopropylacrylamide (NIPAAM, 0.95 g), 2-ethylhexyl acrylate (0.05 g), and 2,2'-Dicumyl peroxide (0.01 g) were dissolved in 10 mL dioxane. The solution was degassed with nitrogen for 15 minutes and then heated to 70° C. for 16 hours under inert atmosphere. The reaction mixture was allowed to cool and then added to hexanes, dropwise. The precipitate was filtered, washed with hexanes, and dried to yield the copolymer.

Example 8

Procedure to Insert a Co-Polymeric Composition into the Tear Ducts of a Subject

The copolymer is inserted into the superior, inferior, or both lacrimal canals, wherein the actuation occurs transitioning the material from liquid to solid. The insertion of the copolymer involves: (1) cooling the thermally-responsive hydrogel below the temperature at which it becomes elastic, (2) injecting the liquid material via an applicator tool into the lacrimal canal, (3) allowing the material to flow into the lacrimal canal conforming to the shape of the channel, and (4) allowing the material to heat to body temperature, wherein the material solidifies in the shape of the ocular channel.

Example 9

Procedure to Remove a Co-Polymeric Composition from the Tear Ducts of a Subject

The co-polymeric composition is removed by administering cold saline to the tear ducts. The tear ducts are flushed with cold saline for approximately 5-10 minutes. The co-polymeric composition exits into the nose or throat.

Example 10

Procedure to Remove a Co-Polymeric Composition from the Tear Ducts of a Subject

The material may be removed through physical means using a handheld removal device, such as forceps, tweezers, and a cotton-tipped applicator. A magnifying instrument or the naked eye is used to locate the co-polymeric composition. A handheld removal device is applied to the visible portion of the co-polymeric composition. The handheld removal device grasps, tugs, or moves the visible portion of the co-polymeric composition out of the tear duct.

Example 11

Hydrogel of Copolymer NIPAM:Butylacrylate (30% Solution)

The copolymer NIPAM:Butylacrylate (95%:5% w/w; molecular weight: $M_n$ 30,000) was purchased from Sigma Aldrich. A 30% solution of the copolymer (hydrogel) was prepared by dissolving the copolymer in DI water by using a horn sonicator for approximately 2 days (30:70 w/w of copolymer:water). Alternatively, the 30% solution of the copolymer can be prepared by dissolving the copolymer in DI water by mixing the solution at room temperature for approximately 1 week or until dissolved. The hydrogel underwent ethylene oxide processing to sterilize the solution.

Example 12

Investigate the Local Tolerability of a Thermo-Responsive Punctual Plug for the Treatment of Dry Eye in Rabbits Local tolerability, toxicity, safety and inflammatory response of a thermo-responsive plug ("test article") in the tear duct in a rabbit model were evaluated. The thermo-responsive hydrogel described in Example 11 was used in the study.

Methods.

Seven New Zealand white rabbits were used in this study. The rabbits were adult male rabbits (greater than 6 months of age), weighing about 4.5-5.5 kg. The rabbits were housed separately during all phases of the study. Rabbits were housed adjacent to each other thus providing social interaction of sight and smell of other rabbits. The rabbits were provided the opportunity for exercise in the cage and at their leisure. The caging units were changed daily to remove feces and urine present in the waste collection pans. All housing units were larger than the specified minimum requirements as outlined in NRC's Guide for the Care and Use of Laboratory Animals 8th Edition. Animals were fed a commercial certified high-fiber rabbit diet. Water was provided ad libitum for all animals at all times, delivered via water bottles with a lixit system. The drinking water used for animals is private well water and has historically not compromised animal health or study results. The rabbits were placed into quarantine status for at least 7 days prior to surgery.

Dosing of the rabbits was performed while under deep sedation. Anesthesia was induced using a Ketamine and Xylazine cocktail (about 35 mg/kg and 4 mg/kg respectively) given IM. A peripheral ear vein was identified and the skin above the vessel was prepped using alcohol prep. An intravenous catheter was placed and secured using tape and gauze. Isoflurane in oxygen (to effect approximately 1-4%) was administered via face mask for maintenance anesthesia. Anesthesia monitoring consisted of pulse rate, respiratory rate, and pulse oximetry (SpO2).

Following the induction of anesthesia, the animal's medial canthus of the eyes was prepared for the surgery by clipping the hair. Once the hair was clipped the site was rinse with saline. The rabbit were placed in sternal recumbancy on a warming blanket. Anesthesia maintained using isoflurane (to effect, approximately 1-4%) in oxygen on a Bain non-rebreathing circuit using a face mask. The surgical site was prepared again as previously described. Each rabbit received about 40-50 mL of Lactated Ringer's Solution (LRS) delivered IV over the course of the procedure.

Procedure: A drop of proparacaine solution 0.5% was instilled into the right eye. The tear duct was cannulated with a needless 22 to 24 g catheter trimmed to approximately 5 mm and 100 microliters of the test article was instilled into the right tear duct.

Once the test article was instilled, anesthesia was terminated, and the animal was allowed to breathe oxygen for 5-10 minutes.

The test article was reconstituted as directed and stored in the refrigerator (about 2-6° C.) until ready to use. On the day of the study, about 100-200 μL of the test article was drawn up into fresh 1 mL syringes. A 22 or 24-gauge intravenous catheter was trimmed to a length of about 5 mm using sterile scissors. The catheter was then attached to the syringe containing test article and primed. The syringes were stored on ice until ready to dose.

At the time of dosing, the medial canthus was retracted to identify the medial lacrimal duct. Once identified, the catheter tip was placed into the duct and the plunger depressed to inject the test article into the duct. In some cases the test article was visible appearing as a white, thick substance. In some cases, successful deployment was difficult to confirm visually but was assumed.

Observations of the first deployment include: (1) keep the test article cold to prevent solidification in the catheter, (2) use a leur lock syringe to prevent the catheter dislodgement from the syringe, and (3) proper tip insertion and deployment into the medial lacrimal duct.

The control eye (contralateral eye) received saline only. The rabbits were given the test article into the right eye. After administration, the eye exams were conducted twice to check for ocular heath.

For the secondary procedure an ophthalmic examination was performed on post-operative day 1 and post-operative day 7 and results were documented.

Tissue specimens, including tear duct and surrounding tissue from each animal fixed in 10% neutral buffered formalin, were tested. At trimming, the tear ducts could not be identified on gross evaluation and longitudinal sections were taken from each tissue specimen for histologic evaluation. The trimmed tissues were processed through graded alcohols, cleared in xylene, embedded in paraffin, sectioned at 5 microns and stained with H&E for light microscopic evaluation.

Results.

Schirmer tear test (STT) was evaluated on both eyes pre-operatively, and on post-operative day 1 and post-operative day 7 after the procedure.

The results are summarized in Table 2 below.

TABLE 2

Summary of the ophthalmic health exams

| Animal | Time Point | STT Treatment | STT Control |
|---|---|---|---|
| 1 | Pre-Op | 13 mm | 12 mm |
|  | POD 1 | 16 mm | 12 mm |
|  | POD 7 | 14 mm | 9 mm |
| 2 | Pre-Op | 12 mm | 13 mm |
|  | POD 1 | 18 mm | 13 mm |
|  | POD 7 | 14 mm | 10 mm |
| 3 | Pre-Op | 10 mm | 12 mm |
|  | POD 1 | 16 mm | 14 mm |
|  | POD 7 | 15 mm | 15 mm |
| 4 | Pre-Op | 13 mm | 14 mm |
|  | POD 1 | 10 mm | 10 mm |
|  | POD 7 | 10 mm | 8 mm |
| 5 | Pre-Op | 10 mm | 12 mm |
|  | POD 1 | 9 mm | 16 mm |
|  | POD 7 | 15 mm | 14 mm |
| 6 | Pre-Op | 13 mm | 12 mm |
|  | POD 1 | 13 mm | 11 mm |
|  | POD 7 | 15 mm | 15 mm |
| 7 | Pre-Op | 10 mm | 15 mm |
|  | POD 1 | 14 mm | 14 mm |
|  | POD 7 | 13 mm | 11 mm |

The POD 1 and POD 7 observations were performed after the test article deployment.

Schirmer Test Results.

Schirmer's test determines whether the eye produces enough tears to keep it moist. This test is used when a person experiences very dry eyes. It poses no risk to the subject. A negative (more than 10 mm of moisture on the filter paper in approximately 5 minutes) test result is normal. Both eyes normally secrete the same amount of tears. Schirmer's test uses paper strips inserted into the eye for several minutes to measure the production of tears. Frequently, this test consists of placing a small strip of filter paper inside the lower eyelid (inferior fornix). The eyes are closed for approximately 5 minutes. The paper is then removed and the amount of moisture is measured. Sometimes a topical anesthetic is placed into the eye before the filter paper to prevent tearing due to the irritation from the paper. The use of the anesthetic ensures that only basal tear secretion is being measured. This technique measures basic tear function. The results are "normal" when there is ≥15 mm wetting of the paper after 5 minutes, "mild" when there is 14-9 mm wetting of the paper after 5 minutes, "moderate" when 8-4 mm wetting of the paper after 5 minutes, "severe" when there is <4 mm wetting of the paper after 5 minutes.

Figure 6:
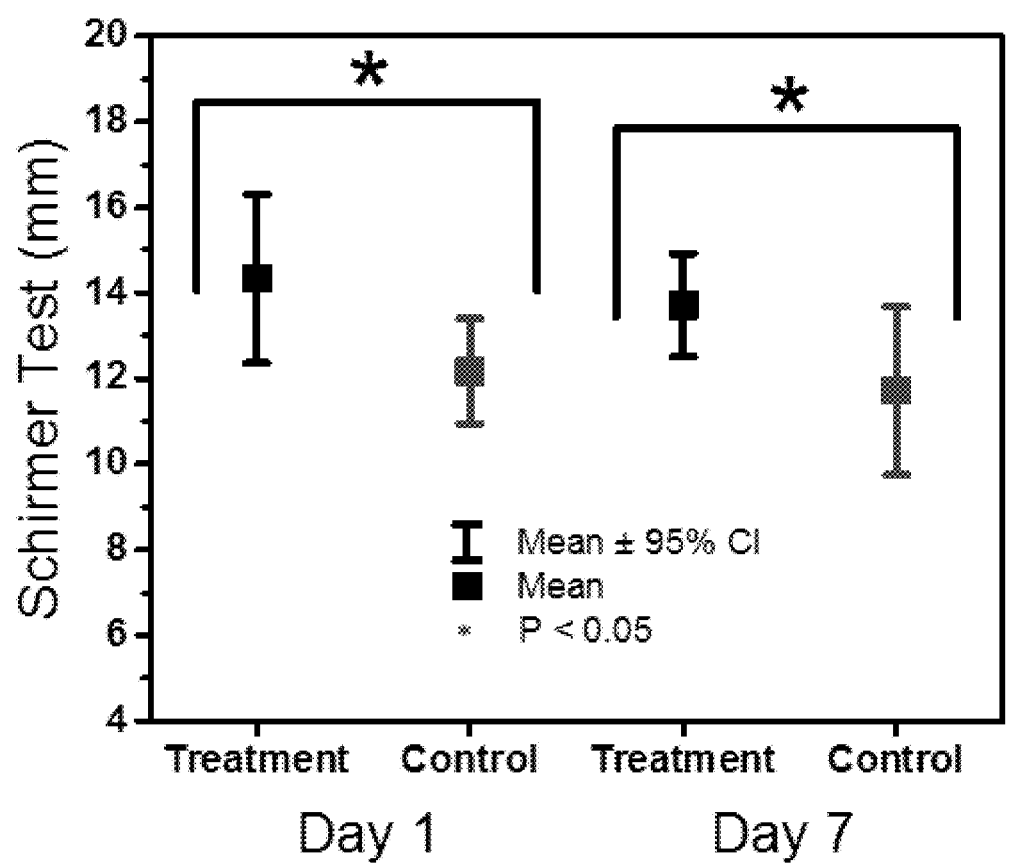
FIG. 6 provides a summary of the Schirmer tests results from an animal trial where the subjects were administered a thermoresponsive punctal plug. The subjects were evaluated at day 1 and day 7.

As shown in FIG. 6, the eyes that were administered the test article (treatment) produced more tears than the eyes that were not (control). Schirmer tests were performed at 1 and 7 days. Statistically significant increases in STT were observed at both time points. On Day 1, the treatment group had an average of ≥14 mm wetting of the paper after approximately 5 minutes, while the control group had an average of approximately 12 mm wetting of the paper after approximately 5 minutes. On Day 7, the treatment group had an average of approximately 13.5 mm wetting of the paper after approximately 5 minutes, while the control group had an average of approximately 11.5 mm wetting of the paper after approximately 5 minutes.

Histology Results.

Histologic evaluation included evaluation for any evidence of adverse injury or toxic effect in the lacrimal drainage system and surrounding tissue. Additionally, each lacrimal duct and any glandular tissue (if provided) were evaluated using a semi-quantitative grading scheme as shown in Table 1.

TABLE 1

Semi-quantitative grading system

| Score | Classification | Description |
|---|---|---|
| 0 | No histologic change | The tissue is within normal histologic limits |
| 1 | Minimal | Histologic changes are patchy and there is a negligible change |
| 2 | Mild | Histologic changes are a notable feature but not disrupting a significant amount of the normal tissue architecture |
| 3 | Moderate | Histologic changes are multifocal to diffuse and disrupting the normal tissue architecture |
| 4 | Severe | Histologic changes are diffuse and obliterating much of the normal tissue architecture |

The histologic features, including necrosis, acute inflammation (i.e. presence of neutrophils), chronic inflammation (i.e. presence of lymphocytes, plasma cells, macrophages), fibrosis, epithelial hyperplasia and epithelial metaplasia, were graded in duct and immediately surrounding tissue, and glandular tissue (separate scores).

On necropsy, there were no gross lesions to note with any rabbit and macroscopically, the test article was not visible. In at least one case, one rabbit had test article visible at the time of necropsy.

Post necropsy histological analysis was performed on samples from the duct and immediately surrounding tissue, and glandular tissue. The results indicate no substantial difference between the left and right eyes and there was no evidence of necrosis, acute inflammation, fibrosis, epithelial metaplasia or toxicity in the ducts or adjacent tissue associated with the test material. There was no evidence of necrosis, acute inflammation, fibrosis, epithelial changes or toxicity in the glandular tissue associated with the test material.

Ductular structures were identified in 13 of the 14 tissue specimens and the predominant histologic finding was minimal to small numbers of primarily lymphocytes infiltrating the immediately adjacent tissue sometimes associated with minimal epithelial hyperplasia. In particular, of the 14 tissues samples of the duct and immediately adjacent tissue, the following was determined: (1) for necrosis, 13 samples received a score of "0" (no histologic change) and 1 sample was not present for evaluation; (2) for acute inflammation, 13 samples received a score of "0" (no histologic change) and 1 sample was not present for evaluation; (3) for chronic inflammation, 7 samples received a score of "2" (mild), 6 samples received a score of "1" (minimal) and 1 sample was not present for evaluation; (4) for fibrosis, 13 samples received a score of "0" (no histologic change) and 1 sample was not present for evaluation; (5) for epithelial hyperplasia, 6 samples received a score of "1" (minimal), 7 samples received a score of "0" (no histologic change) and 1 sample was not present for evaluation; and (6) for epithelia metaplasia, 13 samples received a score of "0" (no histologic change) and 1 sample was not present for evaluation. There was no substantial difference between the left and right eyes and there was no evidence of necrosis, acute inflammation, fibrosis, epithelial metaplasia or toxicity in the ducts or adjacent tissue associated with the test material. The significance of the low grade chronic inflammation is uncertain. While it could be associated with introduction or presence of the test material, low grade infiltrates of lymphocytes and plasma cells is a common histologic finding in adult animals (unpublished observation) and this response may be an incidental finding unrelated to the test material.

Nine of the fourteen treatment sites included a small amount of glandular tissue either in the eyelid or submitted as a separate tissue specimen. This glandular tissue was histologically consistent with lacrimal gland and 5 of the 9 samples showed a minimal infiltrate of lymphocytes and plasma cells with no substantial difference between the left and right eyes. In particular, of the 14 tissues samples of the glandular tissue, the following was determined: (1) for necrosis, 9 samples received a score of "0" (no histologic change) and 5 samples were not present for evaluation; (2) for acute inflammation, 9 samples received a score of "0" (no histologic change) and 5 samples were not present for evaluation; (3) for chronic inflammation, 5 samples scored "1" (minimal), 4 samples received a score of "0" (no histologic change) and 5 samples were not present for evaluation; (4) for fibrosis, 9 samples received a score of "0" (no histologic change) and 5 samples were not present for evaluation; (5) for epithelial hyperplasia, 9 samples received a score of "0" (no histologic change) and 5 samples were not present for evaluation; and (6) for epithelia metaplasia, 9 samples received a score of "0" (no histologic change) and 5 samples were not present for evaluation. This degree of cellular infiltrate is a common histologic finding in adult animals and likely represents an incidental finding unrelated to the test material. There was no evidence of necrosis, acute inflammation, fibrosis, epithelial changes or toxicity in the glandular tissue associated with the test material.

The test article did not show signs of localized or systemic inflammation or pathology. No adverse clinical events were seen over the course of this study.

Example 13

Human (Small Study)

Safety and tolerability of a thermo-responsive plug ("test article") in the tear duct in a human model were evaluated. The thermo-responsive hydrogel described in Example 11 was used in the study.

Methods.

Five healthy human patients were used in the study. The human patients were ≥18 years old and individuals of any sex. The human patients did not have any of the following characteristics: active infection of the cornea or ocular surface, history of refractive surgery, clinically significant eyelid disease, history of neuropathic paralysis, or inadequately controlled clinical conditions of comorbidity that can contribute to ocular signs and symptoms that are not directly related with dry eye based on clinical examination, such as blepharitis or allergies.

A dry eye symptom (OSDI) questionnaire was administered to the human patients. A complete ophthalmologic evaluation with visual acuity measurement (AV), evaluation with slit lamp, Schirmer test for 5 minutes and evaluation of corneal fluorescein staining was performed.

After the examination, the test article was inserted into the left or right tear duct of the patient, at random ("treatment eye"). The contralateral eye was treated with saline, so as to simulate the procedure ("control eye"). The lacrimal ducts were identified and inspected by the administrator, and then a cannula was gently inserted into the duct nasolacrimal in the ventromedial direction. The human patents were monitored and examined following the procedure. The following were measured during the study: Tear meniscus height, Schirmer test, Sicca ocular staining score, OSDI questionnaire. Tests were performed pre and post insertion, 48 hours, 7 days, and 14 days.

At the end of the study (after 14 days), the plug was removed by rinsing with saline cooled to <5° C. and a clearance test of the meniscus with fluorescein comparing both eyes to confirm that the clearance in both eyes were comparable once the tear plug was removed.

Results.

After two weeks of follow up in the 5 healthy human subjects, the following were observed. There were no adverse effects related to implantation and/or presence of the punctal plugs that were observed. One participant reported "feeling" a slight "pressure" or "filling sensation" in the lacrimal plug area. Three participants consistently reported having more tears than usual in the treated eye, as well as more tears in the treated eye than in the contralateral eye. The tear meniscus height can be used to estimate tear volume. A tear meniscus height less than 0.25 mm is suggestive of dry eye. Lacrimal meniscus height measurements (OCT) were consistently more variable in the treated eyes than in the untreated ones, as described in FIG. 10A. In general, where there was variability in tear meniscus in treated eyes it was due to a meniscus height increase. When all (pooled) meniscus height were compared from treated eyes vs. untreated eyes (evaluations 2-5), a significant difference (p=0.14) was not seen. However, given the small sample, this number can be interpreted as a trend. Additionally, comparing healthy eyes before and after insertion of the plug might not contribute to observe larger differences in tear meniscus height before and after the treatment. In all eyes (5) of the treated patients, there was a significant resistance at the time of flushing out the plug with chilled water. A trend towards meniscus height increase in the five cases treated can be seen. Additionally, subjective perceptions from patients confirm these observations. The resistance observed during removal of the plug is also an indicator that the plug created an obstruction, and the plug was firmly adhered.

Schirmer Test Results.

Figure 7A:
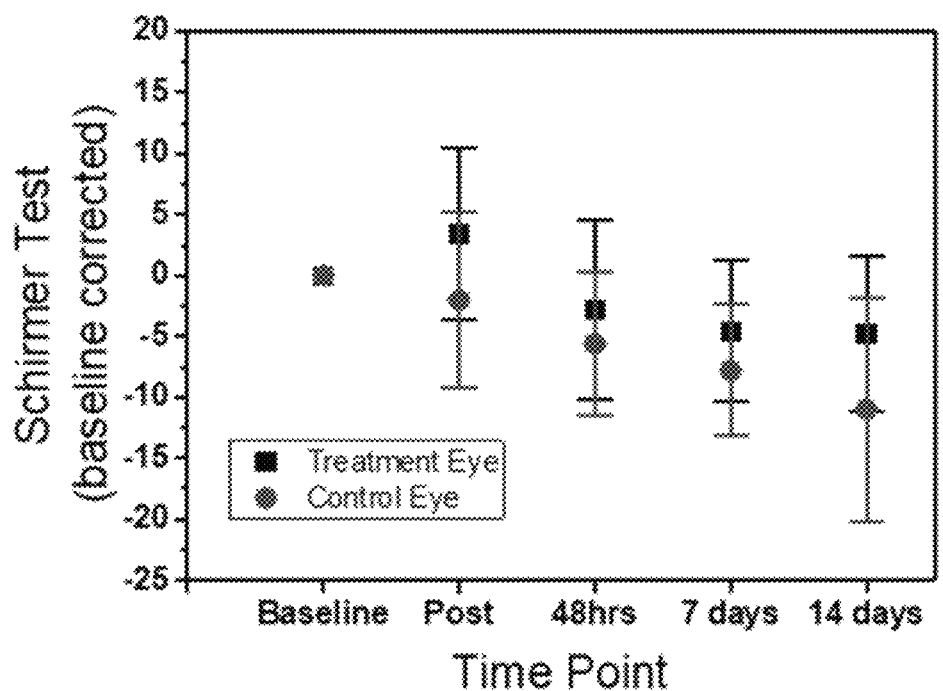
FIG. 7A and FIG. 7B provide a summary of the Schirmer tests results from a human trial where the subjects were administered a thermoresponsive punctal plug. The subjects were evaluated at pre and post insertion, 48 hours, 7 days and 14 days.
Figure 7B:
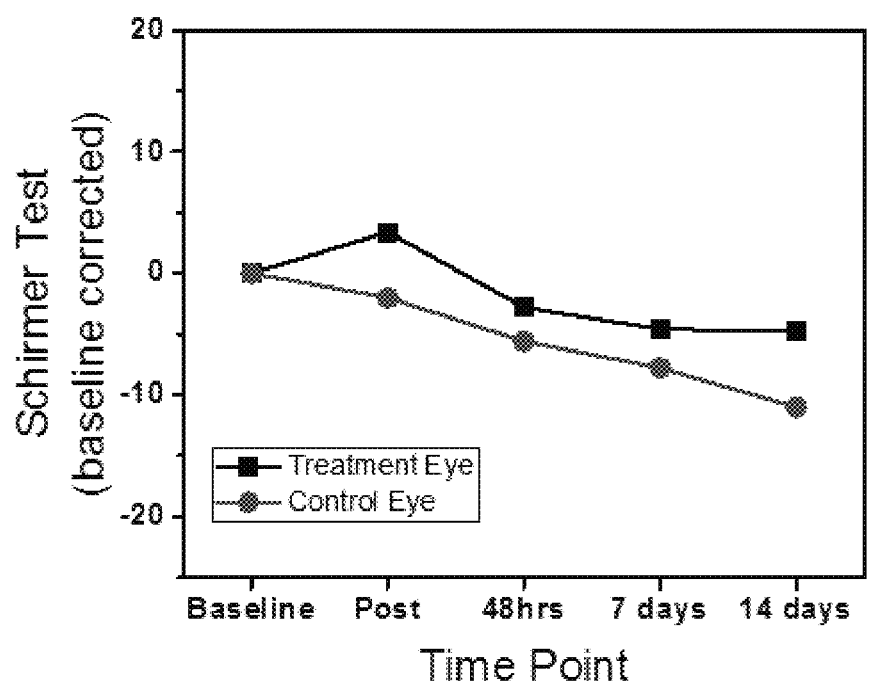
Figure 8A:
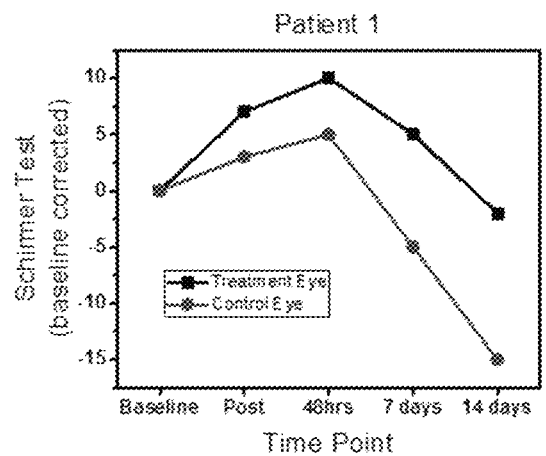
FIG. 8A-FIG. 8E represent the Schirmer test results for each individual subject (patient 1, patient 2, patient 3, patient 4, and patient 5, respectively). Each subject was administered a thermoresponsive punctal plug. The subjects were evaluated at pre and post insertion, 48 hours, 7 days and 14 days.
Figure 8B:
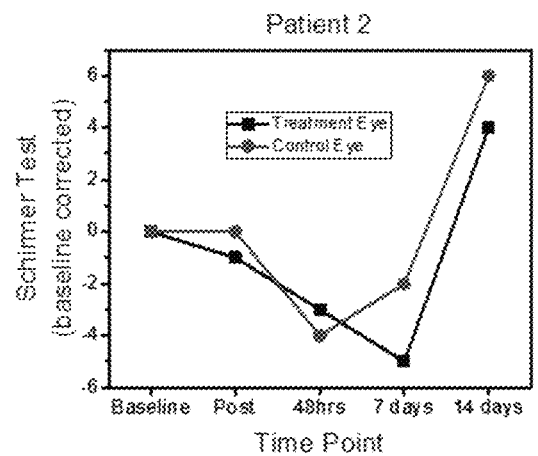
Figure 8C:
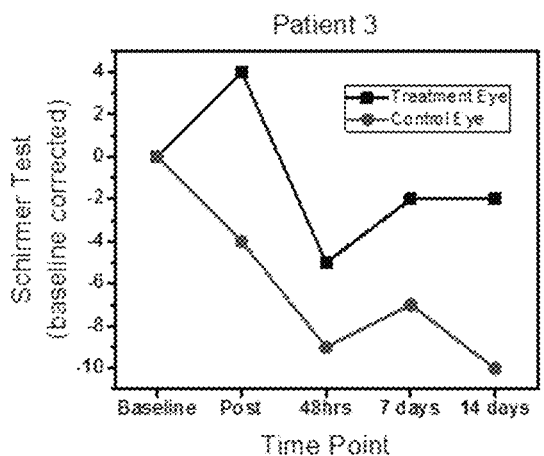
Figure 8D:
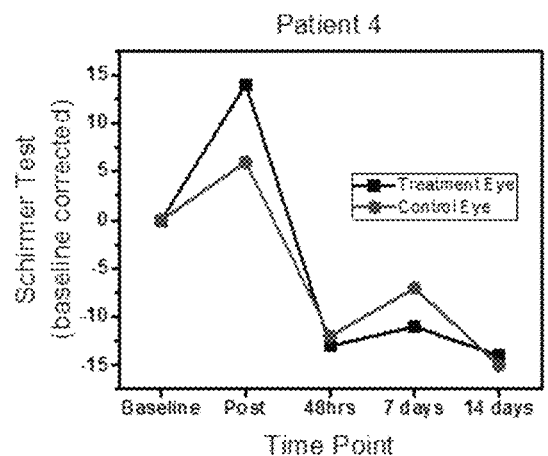
Figure 8E:
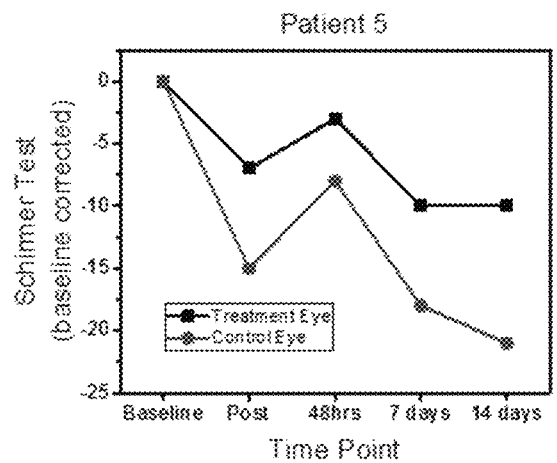

Schirmer tests were performed for the treatment eye and control eye, respectively, for each patient at the determined time points (baseline, post, 48 hours, 7 days, and 14 days). As shown in FIG. 7A and FIG. 7B, the treatment eye showed better tear retention than the control group. On average, an increase in STT of the treatment eye compared to the control eye was observed at all 4 time points. FIG. 8A-FIG. 8E provide the results for the individual patients. Following device insertion, the treatment group had an average increase of 3 mm compared to baseline, while the control group had an average decrease of approximately 2 mm. After 48 hrs, the treatment group had an average decrease of approximately 3 mm relative to baseline, while the control group had an average decrease of approximately 6 mm relative to baseline. After 7 days, the treatment group had an average decrease of approximately 4 mm relative to baseline, while the control group had an average decrease of approximately 8 mm relative to baseline. After 14 days, the treatment group had an average decrease of approximately 5 mm relative to baseline, while the control group had an average decrease of approximately 11 mm relative to baseline.

Figure 9A:
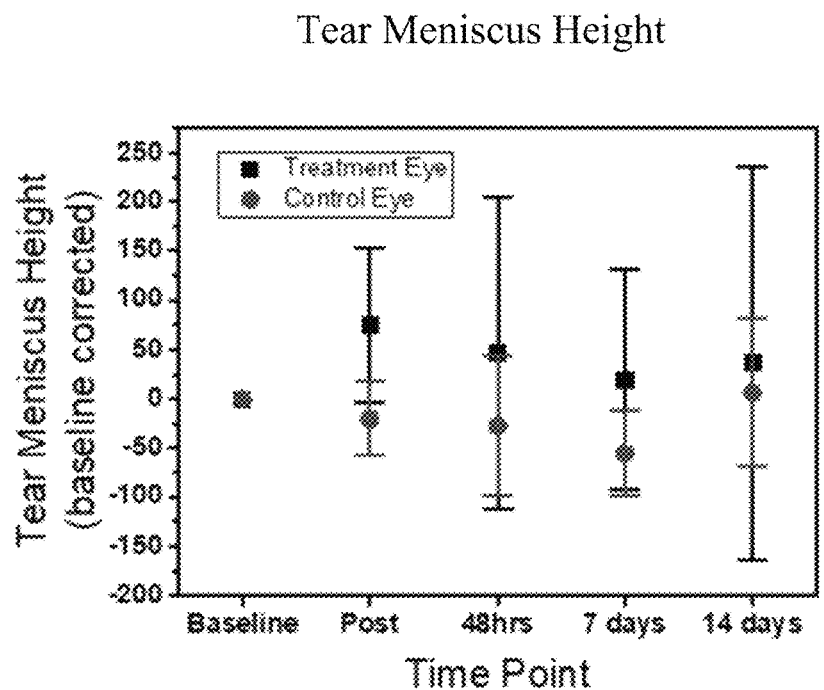
FIG. 9A-FIG. 9C represent the tear meniscus height results from a human trial where the subjects were administered a thermoresponsive punctal plug. The subjects were evaluated at pre and post insertion, 48 hours, 7 days and 14 days.
Figure 9B:
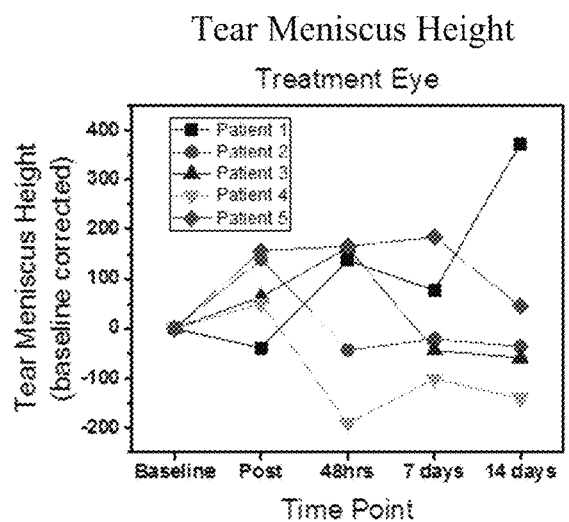
Figure 9C:
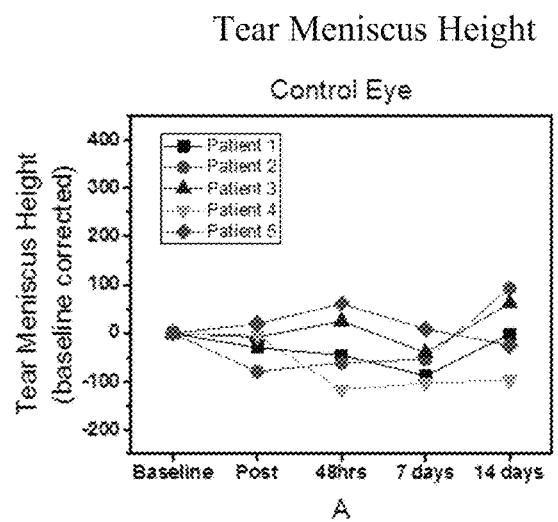

As shown FIG. 9A, the treatment group produced greater tear volume than the control group. On average, increases in tear meniscus height were observed at all 4 time points (post, 48 hours, 7 days, and 14 days). FIG. 9B and FIG. 9C illustrate the tear meniscus height for the treatment eye and control eye, respectively, for each patient at the determined time points (baseline, post, 48 hours, 7 days, and 14 days). Following device insertion, the treatment group had an average increase of 70 μm compared to baseline, while the control group had an average decrease of approximately 20 μm. After 48 hrs, the treatment group had an average increase of approximately 50 μm relative to baseline, while the control group had an average of decrease of approximately 30 μm relative to baseline. After 7 days, the treatment group had an average increase of approximately 20 μm relative to baseline, while the control group had an average of decrease of approximately 50 μm relative to baseline. After 14 days, the treatment group had an average increase of approximately 40 μm relative to baseline, while the control group had an average of increase of approximately 5 μm relative to baseline.

Example 14

Human (Large Study)

Safety and tolerability of a temperature-adaptive lacrimal plug ("test article") in the tear duct in a human model is evaluated. The thermo-responsive hydrogel described in Example 11 was used in the study.

The study evaluates tolerability, adverse events, the rejection of dry eye symptoms, the reduction of corneal staining with fluorescein, and the increase in the height of the tear meniscus. The study is conducted for 14 days with 20 patients. The patients are divided into two groups: 10 healthy participants ("Group A") and 10 patients with dry eye syndrome ("Group B"). Each group may be extended in case of loss of patient follow-up in case of situations not related to directly attributable adverse events to the evaluated device. The study is carried out following the guidelines given by the Declaration of Helsinki (revised in South Africa in 1996).

For Group A, the patients can be individuals of any sex and must be 18 years old or older. For Group B, the patients can be individuals of any sex, must be 18 years old or older, must have a corneal staining with fluorescein of 6 or more (NEI), and must have a Schirmer test of less than 10 mm. Patients with any of the following are excluded from the study: active infection of the cornea or ocular surface, history of refractive surgery, clinically significant eyelid disease, history of neuropathic paralysis, inadequately controlled clinical conditions of comorbidity that can be contribute to ocular signs and symptoms that are not directly related with dry eye based on clinical examination, such as blepharitis or allergies.

A random sampling of healthy individuals in Group A will be conducted. A random sampling of consecutive patients in Group B will be conducted. In each group, at the same time, the treatment will be applied to one eye and the contralateral eye will serve as untreated control.

A dry eye symptom (OSDI) questionnaire will be administered. Next, will perform a complete ophthalmologic evaluation with visual acuity measurement (AV), evaluation with slit lamp, Schirmer test without anesthesia for 5 minutes and evaluation of corneal fluorescein staining. If possible, it will be measured the height, area and radius of curvature of the superior and inferior tear meniscus.

After the exam, a thermo-adaptable tear plug will be inserted at the point Right or left lower tear of the patient, the laterality of the cap will be randomly selected by flipping a coin. A procedure will be performed simulated in the other eye so that the patient does not know the side of the lacrimal dot occluded The lacrimal duct will be identified and inspected by the doctor. Once the duct is identified, the cannula will be gently inserted into the duct nasolacrimal in the ventromedial direction.

Once the placement is confirmed, the eye selected for treatment will receive the Test Item at the point lacrimal according to the recommendations of preparation of the device. The Control eye will receive a small injection of saline only.

After 15 minutes after the procedure, an evaluation will be made ophthalmologic monitoring with visual acuity measurement, evaluation with slit lamp, Schirmer test at 5 minutes, fluorescein staining and exploration of the posterior segment with aerial lens. If possible, the height, area and the radius of curvature of the superior and inferior tear meniscus will be measured at 5, 15, 30 and 60 minutes after insertion.

After 48 hours, the patient will return for an ophthalmologic evaluation of follow-up with visual acuity measurement, evaluation with lamp cleft, Schirmer test at 5 minutes, fluorescein staining. If possible, the height, area and radius of curvature of the tear meniscus will be measured upper and lower. After 7 days, the patient will return for an evaluation ophthalmologic monitoring with visual acuity measurement, evaluation with slit lamp, Schirmer test at 5 minutes, fluorescein staining. If possible, the height, area and radius of curvature of the tear meniscus should be measured upper and lower. After 14 days, the patient will return for an evaluation ophthalmologic monitoring with visual acuity measurement, evaluation with slit lamp, Schirmer test at 5 minutes, fluorescein staining. If possible, the height, area and radius of curvature of the meniscus will be measured upper and lower lacrimal.

At the end of the study the cap will be removed by rinsing with saline cooled (<5° C.) and a clearance test of the meniscus with fluorescein comparing both eyes to confirm that the clearance in both eyes is comparable once the tear plug is removed.

The main variable of the study is the height of the lacrimal meniscus. The independent variables include age and sex. The unit of measurement of the variable include the following: age (years), sex, ocular stain score with fluorescein, lacrimal meniscus height (μm), Schirmer test (mm), dry eye symptoms (0-100 points). The measurement instruments include: OSDI questionnaire, optical coherence tomograph (OCT), Schirmer's strip, slit lam and fluorescein staining, and OSDI dry eye symptoms questionnaire.

The comparison between the questionnaires will be done using Bland-Altman graphics and comparison of means. For Bland-Altman graphics, the differences between the group of eyes treated and the control group (untreated eyes) will be plotted comparing the average of both groups, to evaluate the agreement between the full range of measurements. A Perfect combination implies that the difference between both teams will be zero. The Concordance limits (LC) will be calculated as the average difference between the measurements with each equipment ±1.96 standard deviations (SD) of the differences. A standard deviation of 2.00 is, by definition, the range of agreement between the techniques with the lowest value indicating a high concordance. For comparison of means, the comparison of the means will be made through Student's t-test or non-parametric Wilcoxon test. The comparison between the ocular staining score with fluorescein, the test of Schirmer and the lacrimal meniscus height will be made using comparison of the means—the comparison of the means will be made through of the Student's t-test or the non-parametric Wilcoxon test.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating dry eye in a subject, the method comprising:
   (a) injecting a hydrogel comprising stimuli-responsive polymer into a tear duct of the subject, wherein the stimuli-responsive polymer comprises copolymer of N-isopropylacrylamide and butylacrylate, wherein the N-isopropylacrylamide is at least 98 wt % of the copolymer and the butylacrylate is at most 2 wt % of the copolymer;
   (b) permitting said hydrogel to conform to the shape of the tear duct;
   (c) activating said stimuli-responsive polymer in the hydrogel with a trigger, wherein said trigger initiates a phase transition of said stimuli-responsive polymer from a liquid or semi-liquid to a solid or semi-solid, thereby forming a plug in the tear duct to treat said dry eye in the subject; and
   (d) removing the plug after treatment of said dry eye by applying a stimulus to the plug so that the viscosity of the stimuli-responsive polymer in the plug decreases.

2. The method of claim 1, wherein said stimuli-responsive polymer at least partially fills said tear duct.

3. The method of claim 1, wherein said trigger is a change in temperature or pH.

4. The method of claim 1, wherein said trigger is temperature.

5. The method of claim 1, wherein activating said stimuli-responsive polymer involves heating said stimuli-responsive polymer.

6. The method of claim 1, wherein said stimuli-responsive polymer is a liquid or semi-liquid prior to injecting into the tear duct of the subject.

7. The method of claim 1, wherein said stimuli-responsive polymer is administered in an aqueous solution.

8. The method of claim 1, wherein said stimuli-responsive polymer further comprises at least one excipient.

9. The method of claim 1, wherein said stimuli-responsive polymer further comprises at least one additive.

10. The method of claim 1, wherein said stimuli-responsive polymer is injected into the tear duct of the subject in an aqueous solution.

11. The method of claim 10, wherein said stimuli-responsive polymer has a concentration of about 10 weight percent to about 60 weight percent in said aqueous solution.

12. The method of claim 10, wherein said stimuli-responsive polymer has a concentration of about 20 weight percent to about 50 weight percent in said aqueous solution.

13. The method of claim 10, wherein said stimuli-responsive polymer has a concentration of about 30 weight percent to about 40 weight percent in said aqueous solution.

14. The method of claim 13, wherein said stimuli-responsive polymer has a concentration of about 30 weight percent in said aqueous solution.

15. The method of claim 1, wherein said stimuli-responsive polymer has a lower critical solution temperature from about 10° C. to about 35° C.

16. The method of claim 1, further comprising maintaining said stimuli-responsive polymer at a temperature at least approximately below the lower critical solution temperature of said stimuli-responsive polymer prior to injecting.

17. The method of claim 5, wherein said heating is applied from said subject's body temperature.

18. The method of claim 1, wherein the tear duct comprises the puncta, the canaliculi, the lacrimal sac, or the lacrimal duct.

19. The method of claim 1, wherein said subject is human or animal.

20. The method of claim 1, further comprising inserting a dilator into said tear duct and dilating said tear duct prior to said injecting.

21. The method of claim 1, wherein said method is effective in increasing tear moisture or volume in the eye.

22. The method of claim 1, wherein the N-isopropylacrylamide is from 98 wt % to 99 wt % of the copolymer and the butylacrylate is from 1 wt % to 2 wt % of the copolymer.

23. The method of claim 1, wherein the N-isopropylacrylamide is 99 wt % of the copolymer and the butylacrylate is 1 wt % of the copolymer.

24. The method of claim 1, wherein said stimuli-responsive polymer has a lower critical solution temperature from about 27° C. to about 31° C.

25. The method of claim 1, wherein said stimuli-responsive polymer is cross-linked.

26. The method of claim 1, wherein said stimuli-responsive polymer is sterilized.

27. The method of claim 1, wherein the plug is exposed to a fluid comprising water, saline, or mineral oil in step d).

28. The method of claim 1, wherein the plug is exposed to a fluid having a temperature less than 15° C. in step d).

* * * * *